US009931462B2

United States Patent
(12) United States Patent
Heller et al.

(10) Patent No.: US 9,931,462 B2
(45) Date of Patent: Apr. 3, 2018

(54) ELECTRO-OSMOTIC PUMPS WITH ELECTRODES COMPRISING A LANTHANIDE OXIDE OR AN ACTINIDE OXIDE

(71) Applicant: Board of Regents of the University of Texas System, Austin, TX (US)

(72) Inventors: Adam Heller, Austin, TX (US); Rajaram K. Nagarale, Karnataka (IN)

(73) Assignee: BOARD OF REGENTS OF THE UNIVERSITY OF TEXAS SYSTEM, Dallas, TX (US)

( * ) Notice: Subject to any disclaimer, the term of this patent is extended or adjusted under 35 U.S.C. 154(b) by 312 days.

(21) Appl. No.: 13/965,345

(22) Filed: Aug. 13, 2013

(65) Prior Publication Data

US 2014/0088506 A1 Mar. 27, 2014

Related U.S. Application Data

(60) Provisional application No. 61/704,268, filed on Sep. 12, 2012.

(51) Int. Cl.

*A61M 5/142* (2006.01)
*F04D 13/06* (2006.01)
(Continued)

(52) U.S. Cl.

CPC ....... *A61M 5/14248* (2013.01); *F04B 19/006* (2013.01); *F04D 13/06* (2013.01);
(Continued)

(58) Field of Classification Search

CPC ............. A61M 5/142; A61M 2005/145; F04B 19/006; Y10T 428/249; G01N 27/44756; G01N 27/44752; F04D 13/06

See application file for complete search history.

(56) References Cited

U.S. PATENT DOCUMENTS 4,158,085 A * 6/1979 Bilhorn ......................... 429/130
5,628,890 A 5/1997 Carter et al.
(Continued)

FOREIGN PATENT DOCUMENTS

EP 2065353 A1 6/2009
JP 2008-074677 4/2008
(Continued)

OTHER PUBLICATIONS

Shin et al. (Drug Deliv. and Transl. Res. (2011) 1:342-347).*
(Continued)

*Primary Examiner* — Alexander S Noguerola
(74) *Attorney, Agent, or Firm* — Baker Botts L.L.P.

(57) ABSTRACT

The present disclosure relates, according to some embodiments, to methods, devices, and systems for fluid delivery to a subject using pumps, for example, non-gassing, direct current (DC), electro-osmotic pumps. In some embodiments, delivery of an aqueous fluid may be achieved by contacting the aqueous liquid with an electro-osmotic pump comprising (i) a cathode (e.g., a cathode comprising porous carbon coated with a cerium oxide-comprising coating), (ii) an anode (e.g., an anode comprising porous carbon coated with a cerium oxide-comprising coating), and (iii) a ceramic membrane (e.g., a ceramic membrane formed by fusing uncoated silica spheres, phosphosilicic-acid-coated fused silica spheres, or borosilicic-acid-coated fused silica spheres, wherein the fused spheres are randomly packed between the cathode and the anode) and/or optionally applying (a) a constant potential difference or constant voltage between the anode and the cathode of from about 0.1 V to about 3 V between the anode and the cathode of from about 0.1 V to about 3 V such that the aqueous liquid is pumped or (b) constant current to cause a potential difference
(Continued)

between the anode and the cathode of from about 0.1 V to about 3 V such that the aqueous liquid is pumped.

28 Claims, 17 Drawing Sheets

(51) Int. Cl.
*F04B 19/00* (2006.01)
*G01N 27/447* (2006.01)
*A61M 5/145* (2006.01)

(52) U.S. Cl.
CPC .............. *A61M 2005/14513* (2013.01); *G01N 27/44756* (2013.01); *Y10T 428/249981* (2015.04)

(56) References Cited

U.S. PATENT DOCUMENTS

| | | | | |
|---|---|---|---|---|
| 5,820,551 | A | 10/1998 | Hill et al. | |
| 6,143,164 | A | 11/2000 | Heller et al. | |
| 6,592,745 | B1 | 7/2003 | Feldman et al. | |
| 7,086,839 | B2 | 8/2006 | Kenny et al. | |
| 7,231,839 | B2 | 6/2007 | Huber et al. | |
| 7,235,164 | B2 | 6/2007 | Anex et al. | |
| 7,559,356 | B2 | 7/2009 | Paul et al. | |
| 7,695,603 | B2 | 4/2010 | Paul et al. | |
| 9,168,527 | B2 | 10/2015 | Robinson et al. | |
| 2002/0077676 | A1* | 6/2002 | Schroeppel et al. | 607/75 |
| 2004/0074768 | A1* | 4/2004 | Anex | F04B 17/00 204/294 |
| 2004/0101421 | A1 | 5/2004 | Kenny et al. | |
| 2004/0234378 | A1 | 11/2004 | Lovette et al. | |
| 2005/0233195 | A1* | 10/2005 | Arnold et al. | 429/34 |
| 2006/0044759 | A1* | 3/2006 | Chebiam et al. | 361/699 |
| 2006/0116641 | A1* | 6/2006 | Gordon et al. | 604/141 |
| 2008/0033338 | A1 | 2/2008 | Smith | |
| 2009/0041590 | A1 | 2/2009 | Fuetes et al. | |
| 2009/0260990 | A1 | 10/2009 | Yanagisawa et al. | |
| 2011/0052431 | A1 | 3/2011 | Heldal et al. | |
| 2011/0097215 | A1* | 4/2011 | O'Shaughnessy et al. | 417/48 |
| 2012/0312384 | A1 | 12/2012 | Robinson et al. | |
| 2013/0153425 | A1* | 6/2013 | Puleo et al. | 204/627 |
| 2013/0153797 | A1 | 6/2013 | Puleo et al. | |
| 2013/0156615 | A1 | 6/2013 | Puleo et al. | |

FOREIGN PATENT DOCUMENTS

| | | | |
|---|---|---|---|
| JP | 2008-218019 | | 9/2008 |
| KR | 10-1305149 | B1 | 9/2013 |
| KR | 10-1420360 | B1 | 7/2014 |
| KR | 10-1457629 | | 11/2014 |
| WO | 2011/102801 | A1 | 8/2011 |
| WO | 2011/112723 | | 9/2011 |
| WO | 2014/112726 | A1 | 7/2014 |

OTHER PUBLICATIONS

Torikai et al. (Journal of the Australian Ceramic Society vol. 4911], 2013, 9-14).*

Smit et al., "Electroosmotic Zeta Potential measurement on Single Crystals," Journal of Colloid and Interface Science, vol. 60, No. 2 Jun. 15, 1977.*

JPO computer-generated English language translation of JP 2008-218019 A. Downloaded Nov. 6, 2017.*

International Search Report and Written Opinion, PCT/US2013/054627, dated Jan. 13, 2014, 20 pages.

P. G. Erlandsson and N. D. Robinson, "Electrolysis-reducing electrodes for electrokinetic devices," Electrophoresis, vol. 32, (2011) pp. 784-790.

F. Heuck, P. Van Der Ploeg and U. Staufer, "Deposition and structuring of Ag/AgCl electrodes inside a closed polymeric microfluidic system for electroosmotic pumping," Microelectronic Engineering, vol. 88, (2011), pp. 1887-1890.

W. Shin, S. J. Shin, J. M. Lee, R. K. Nagarale and A. Heller, "A miniature, single use, skin-adhered, low-voltage, electroosmotic pumping-based subcutaneous infusion system," Drug Delivery and Translational Research, vol. 1, (2011), pp. 342-347.

R. K. Nagarale, A. Heller and W. Shin, "A Stable Ag/Ceramic-Membrane/$Ag_2O$ Electroosmotic Pump Built with a Mesoporous Phosphosilicate-on-Silica Frit Membrane," Journal of the Electrochemical Society, vol. 159, No. 1, (2012), p. 14-17.

J. F. Evans and T. Kuwana, "Radiofrequency Oxygen Plasma Treatment of Pyrolytic Graphite Electrode Surfaces," Analytical Chemistry, vol. 49, No. 11 (1977), pp. 1632-1635.

L. Y. Yuan, S. S. Shyu and J. Y. Lai, "Plasma surface treatments of carbon fibers. Part 2: Interfacial adhesion with poly(phenylene sulfide)," Composites Science and Technology, vol. 45, (1992), pp. 9-16.

C. U. Pittman Jr, W. Jiang, G. R. He and S. D. Gardner, "Oxygen Plasma and Isobutylene Plasma Treatments of Carbon Fibers: Determination of Surface Functionality and Effects on Composite Properties," Carbon, vol. 36, Nos. 1-2 ,(1998), pp. 25-37.

E. D. Perakslis, S. D. Gardner and C. U. Pittman Jr., "Surface composition of carbon fibers subjected to oxidation in nitric acid followed by oxygen plasma," Journal of Adhesion Science and Technology,vol. 11, No. 4, (1997), pp. 531-551.

S. Erden, K. K. C. Ho, S. Lamoriniere, A. F. Lee, H. Yildiz and A. Bismarck, "Continuous Atmospheric Plasma Oxidation of Carbon Fibres: Influence on the Fibre Surface and Bulk Properties and Adhesion to Polyamide 12," Plasma Chem. Plasma Process., vol. 30, (2010), pp. 471-487.

K. Okajima, K. Ohta and M. Sudoh, "Capacitance behavior of activated carbon fibers with oxygen-plasma treatment," Electrochimica Acta, vol. 50, (2005), pp. 2227-2231.

W. Shin, E. Zhu, R.K. Nagarale, C.H. Kim, J.M. Lee, S.J. Shin and A. Heller, "Nafion-Coating of the Electrodes Improves the Flow-Stability of the $Ag/SiO_2/Ag_2O$ Electroosmotic Pump," Analytical Chemistry, vol. 83, (2011), pp. 5023-5025.

W. Shin, J. M. Lee, R. K. Nagarale, S. J. Shin and A. Heller, "A Miniature, Nongassing Electroosmotic Pump Operating at 0.5 V," Journal of the American Chemical Society, vol. 133, (2011), pp. 2374-2377.

Shin, W., et al., "Nafion-Coating of the Electrodes Improves the Flow-Stability of the Ag/SiO2/Ag2O Electroosmotic Pump," Analytical Chemistry, Technical Note, (2011), vol. 83, pp. 5023-5025.

Extended European Search Report, EP Application No. 13838627.1, dated May 24, 2016, 7 pages.

Office Action received for Japanese Patent Application No. 2015-533066, dated Jul. 28, 2017; 9 pages.

Office Action received for European Patent Application No. 13838627.1, dated Aug. 4, 2017; 4 pages.

* cited by examiner

FIG. 5F
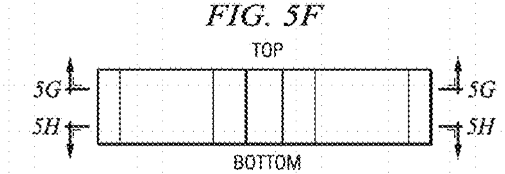
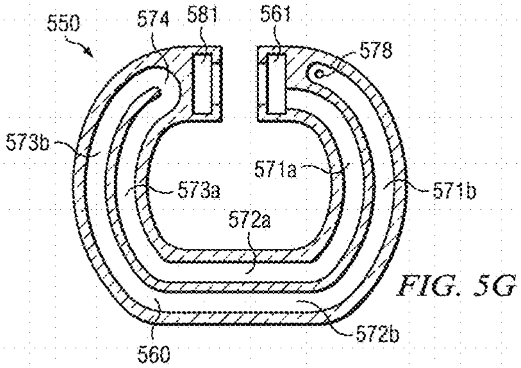
FIG. 5G
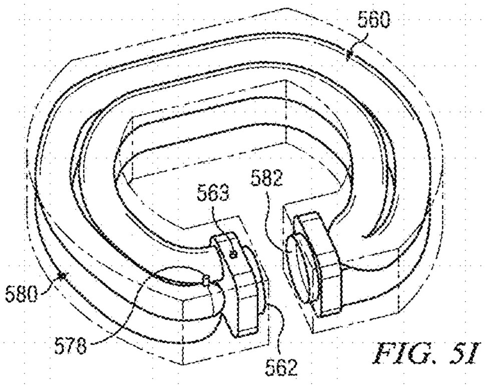
FIG. 5I
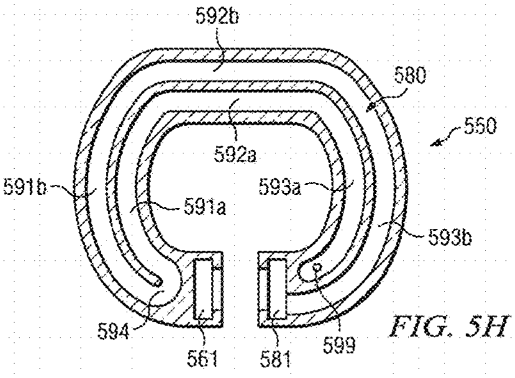
FIG. 5H 800
860
878
876,877
863,864
810
880
856a
883,884
896,897
898
899

800
860
878
876,877
810
880
856a
857a
883,884
896,897
898
899

800
860
878
876,877
810
880
856a
856b
857a
883,884
896,897
898
899

ELECTRO-OSMOTIC PUMPS WITH ELECTRODES COMPRISING A LANTHANIDE OXIDE OR AN ACTINIDE OXIDE

CROSS-REFERENCE TO RELATED APPLICATIONS

This application is claims priority to U.S. Provisional Application No. 61/704,268, filed Sep. 21, 2012, the contents of which are hereby incorporated in their entirety by reference.

FIELD OF THE DISCLOSURE

The present disclosure relates, in some embodiments, to methods, devices, and systems for drug delivery using pumps, for example, non-gassing, direct current (DC), electro-osmotic pumps.

BACKGROUND OF THE DISCLOSURE

Electro-osmotic pumps are mechanically less complex than other pumps; typically they have fewer components, particularly fewer moving components. Small pumps are widely used both in ambulatory and in non-ambulatory drug delivery systems, including systems comprising a skin-adhered drug reservoir and pump. For example, skin-adhered insulin "pumps" are in use. Their pumps are often mechanical. Electro-osmotic pumps for drug delivery have been considered for 40 years or more, but none were sold.

Electro-osmotic pumps that are manufactured and sold are applied in compact bioanalytical systems and in heat pumps. In some of these, the pumps now drive liquids through long and narrow on-chip and off-chip capillaries and through miniature packed chromatographic columns. Pumps have been integrated in silicon chips and are part of lab-on-chip devices. While polymeric ion exchange membranes were used in the early pumps, the more recent pumps have ceramic membranes, particularly of porous silica, although porous silicon and aluminum oxide have also been used. Platinum electrodes, on which water is electrolyzed at the applied high voltages ranging from 3V to 400V, are usually used. Gas bubbles resulting from electrolysis, however, may interfere with the operation of the pumps. Electro-osmotic pumps having ceramic membranes and gas-evolving electrodes have been sold, for example, by NI (Nano Fusion Technologies, Tokyo). Fouling may occur during pump operation due, for example, to migration of ions from the electrodes to the pump's membrane.

SUMMARY

The present disclosure relates, according to some embodiments, to devices, systems, and methods for delivering a composition to a subject (e.g., human and/or animal). According to some embodiments, an electro-osmotic pump system suitable for use, for example, in drug delivery systems, providing stable flow is disclosed. An optionally on-the-skin drug-delivering system may be of low-cost, replaceable and small. In some embodiments, the present disclosure relates to an electro-osmotic pump having lanthanide oxide or actinide oxide comprising electrodes, for example, electrodes comprising cerium oxide nanoparticles. For example, a direct current (DC) electro-osmotic pump may comprise a pair of porous electrodes (e.g., comprising an oxide of a lanthanide or of an actinide) positioned at a distance from each other and a porous membrane comprising a first side and a second side. In some embodiments, a DC component of the applied current or applied voltage causes most of the flow of the pumped fluid in a direct current (DC) electro-osmotic pump. This does not mean or imply that the applied voltage or current has no AC component. According to some embodiments, a membrane may be positioned between the pair of electrodes. In some embodiments, at least a part of the first side of the membrane is in physical contact with one of the electrodes and at least a part of the second side of the membrane is in physical contact with the other electrode.

In some embodiments, one or more electrodes of a non-gassing electro-osmotic pump may include a non-metallic electrical conductor. For example, an electrode may comprise carbon (e.g., carbon paper). An electrode may be substantially free of metal (e.g., substantially free of metallic conductors), according to some embodiments. A substantially metal-free electrode may be operable as an electrode on the basis of one or more non-metallic components, for example, non-metallic electrical conductors.

Easy to make, potentially inexpensive, low voltage, non-water electrolyzing electro-osmotic pumps are disclosed. Such pumps may be used, for example, in drug infusion systems, such as ambulatory drug infusion systems, that are optionally small and skin-adhered. In some embodiments, pumps are simple: they may comprise a porous ceramic "membrane" sandwiched between two porous electrodes. An exemplary membrane is a porous silica comprising membrane, optionally also comprising phosphosilicic acid functions. Water flows when a potential or a current is applied. Pumps including electrodes comprising Ag and $Ag_2O$ were described in patent application WO 2011/112723 and in W. Shin et al *J. Am. Chem. Soc.* 133, 2374-2377 (2011); *Drug Deliv. and Transl. Res.* 1:342-347 (2011); *Analytical Chemistry* 83(12), 5023-5025 (2011) and by R. K. Nagarale et al. *Journal of the Electrochemical Society* 159(1), P 14-P 17 (2012), each of which is incorporated herein in its entirety by reference. Electrodes comprising Ag and $Ag_2O$ may be exhausted during pump operation because, as current passes between the electrodes, the Ag may be electrooxidized and/or the $Ag_2O$ may be electroreduced. Also, dissolving $Ag^+$ ions may contaminate the membranes of the pumps, reducing the pumping rate (flow) and the pumping efficiency, which may in turn shorten the useful life of the battery powering the pump.

Accordingly, a need exists for inexpensive, reliable pumps for delivery of fluids to a subject. For example, a need has arisen for pumps capable of delivering a fluid (e.g., a fluid comprising a drug, allergen, and/or other physiologically relevant compound) to a subject at desired intervals and/or rates (substantially) without fouling. A need has arisen for improved pumps (e.g., electro-osmotic pumps) providing a constant flow when a constant current or potential is applied. In some electro-osmotic pumps, membrane-fouling due to metal ion migration (e.g., silver ion migration) from an electrode may reduce the flow.

An electro-osmotic pump may include electrodes comprising silver and/or silver oxide. According to some embodiments of the present disclosure, an electro-osmotic pump may include electrodes comprising a lanthanide oxide and/or an actinide oxide in place of silver/silver oxide electrodes. For example, an electrode may comprise a nanocrystalline oxide of cerium, thorium and/or praseodymium. In some embodiments, cerium oxide may be preferred. The metal oxide may be a mixed oxide, containing two or more lanthanides or actinides, or one or more lanthanides and one or more transition metals. Other than a metal oxide (e.g., cerium oxide), an electrode may comprise a conductor, such as carbon, and an ion-conducting, preferably proton conducting, polymeric material, such as a sulfonated tetrafluoroethylene based fluoropolymer-copolymer (NAFION®). The average size of the lanthanide oxide or an actinide oxide nanocrystallites may be less than about 50 nm; it can be, for example, 30 nm or less, 20 nm or less, or 10 nm or less. In some embodiments, electrodes may be substantially free of all metal.

A lanthanide oxide or actinide oxide may be insulating or conducting, according to some embodiments. Electrodes may also comprise, in some embodiments, a conductor such as carbon. The durability of the pumps may increase (e.g., greatly increased) relative to pumps made with silver and/or silver oxide electrodes. While pumps made with $Ag/Ag_2O$ electrodes may operate at non-water electrolyzing conditions for about 2±1 hours, pumps of this disclosure with silver-free electrodes, may operate for longer than ~3 hours, longer than ~4 hours, longer than ~5 hours, longer than ~7 hours, longer than ~10 hours, longer than ~20 hours, or longer than ~100 hours.

In pumps made with $Ag/Ag_2O$ electrodes, $Ag^+$ ions may migrate, and their migration and binding to the membrane may reduce flow across the membrane. In the absence of flow-affecting $Ag^+$ ions, the flow through the pumps with silver-free electrodes may be more stable, reproducible, and/or controllable.

The present disclosure relates, in some embodiments, to direct current electro-osmotic pumps comprising a pair of porous electrodes positioned at a distance from each other and a porous membrane (e.g., interposed between the electrodes) comprising a first side and a second side. In some embodiments, a membrane may comprise porous ceramic, for example, a porous ceramic comprising silicon (e.g., vitreous silicon dioxide). At least one electrode may comprise, according to some embodiments, an oxide of a lanthanide or of an actinide. For example, at least one electrode may comprise an oxide of cerium, an oxide of praseodymium, an oxide of thorium or combinations thereof. In some embodiments, both electrodes may be substantially free from all metal. The composition of each electrode in a pump may be the same or different from the other electrode(s) in the pump. For example, both electrodes in a two-electrode pump may comprise an oxide of cerium. At least a part of the first side of the membrane may be in physical contact with one of the electrodes and at least a part of the second side of the membrane is in physical contact with the other electrode in some embodiments. At least one electrode may be substantially free (e.g., free) of a metal selected from silver, platinum, palladium, nickel, copper, tungsten, molybdenum, and combinations thereof. According to some embodiments, at least one electrode may comprise carbon and/or a cation exchanging polymer (e.g., a cation exchanging polymer comprising sulfur atoms, a cation exchanging polymer comprising fluorine atoms, a cation exchanging polymer comprising perfluorinated polysulfonic acid). A direct current electro-osmotic pump may comprise, in some embodiments, a pump fluid (e.g., water).

The present disclosure relates to an electro-osmotic fluid delivery system comprising a direct current electro-osmotic pump and a reservoir. A reservoir may comprise, for example, a pump fluid chamber in fluid communication with the electro-osmotic pump and a delivery fluid chamber in fluid communication with the electro-osmotic pump, according to some embodiments. According to some embodiments, a delivery fluid chamber may be configured as a disposable drug cartridge. A delivery system may be worn by a subject (e.g., adhered to a subject's skin) in some embodiments. An electro-osmotic fluid delivery system may comprise, in some embodiments, a needle or cannula in fluid communication with a delivery fluid chamber and configured for insertion into a subject. A kit may comprise an electro-osmotic fluid delivery system and instructions for administering a drug to a subject using the system. A direct current electro-osmotic pump may comprise, in some embodiments, a porous cathode and a porous anode, each comprising cerium oxide, and a porous ceramic membrane between the cathode and the anode, wherein at least a part of the surface of the membrane is in physical contact with the anode and at least a part of the opposite side of the membrane is in physical contact with the cathode.

According to some embodiments, the disclosure relates to a method to produce an electro-osmotic pump comprising the steps of (a) adding an aqueous solution of phosphoric acid and/or an aqueous solution of boric acid to a suspension of silica microspheres having a diameter between about 0.5 μm and about 3 μm to form a suspension, (b) evaporating the water from the suspension to form a powder, (c) pressing the powder to form a pellet having at least two opposite surfaces, (d) firing the pellet for about 1 to about 6 hours at a temperature from about 700° C. to about 900° C. to form the ceramic membrane, (e) washing the ceramic membrane, (f) drying the ceramic membrane, and/or (g) pressing two porous carbon electrodes coated with cerium oxide-comprising coatings onto opposite surfaces of the ceramic membrane to form an electrode-membrane-electrode sandwich.

In some embodiments, delivery of an aqueous fluid may be achieved by contacting the aqueous liquid with an electro-osmotic pump comprising (i) a cathode (e.g., a cathode comprising porous carbon coated with a cerium oxide-comprising coating), (ii) an anode (e.g., an anode comprising porous carbon coated with a cerium oxide-comprising coating), and (iii) a ceramic membrane (e.g., a ceramic membrane formed by fusing uncoated silica spheres, phosphosilicic-acid-coated fused silica spheres, or borosilicic-acid-coated fused silica spheres, wherein the fused spheres are randomly packed between the cathode and the anode), and/or optionally applying (a) a constant potential difference or constant voltage between the anode and the cathode of from about 0.1 V to about 3 V between the anode and the cathode such that the aqueous liquid is pumped or (b) constant current to cause a potential difference between the anode and the cathode of from about 0.1 V to about 3 V such that the aqueous liquid is pumped.

In some embodiments, an electro-osmotic pump may comprise a layered composition. According to some embodiments a layered composition may comprise: (i) a first layer comprising a porous substrate and a coating contacting at least a portion of the substrate; (ii) a second layer comprising a porous silica matrix; (ii) a third layer comprising a porous substrate and a coating contacting at least a portion of the substrate. In some embodiments, the coating may comprise a ceria, cerium oxide or a combination of ceria and cerium oxide. In some embodiments, at least a portion of the first layer may be in contact with the second layer and at least a portion of the third layer may be in contact with the second layer. In some embodiments, a porous substrate of a composition layer may comprise carbon (e.g., non-woven carbon paper or cloth). In some embodiments, a layered composition may be substantially free (e.g., free) of silver, substantially free (e.g., free) of platinum, or substantially free (e.g., free) of silver and platinum. A layered composition may comprise (e.g., have a coating comprising) a polyanionic membrane (e.g., perfluorosulfonic acid/polytetrafluoroethylene copolymer or a perfluorosulfonic acid/polytetrafluoroethylene copolymer).

An electro-osmotic fluid delivery system may comprise, in some embodiments, (a) an electro-osmotic pump comprising (i) a porous cathode comprising $Ce^{4+}$ ions, (ii) a porous anode comprising $Ce^{3+}$ ions and (iii) a porous ceramic membrane between the cathode and the anode, wherein at least a part of the surface of the membrane is in physical contact with the anode, and at least a part of the opposite side of the membrane is in physical contact with the cathode; (b) a reservoir comprising a pump fluid chamber in fluid communication with the electro-osmotic pump and a delivery fluid chamber in fluid communication with the electro-osmotic pump; (c) a removable controller assembly in electrical communication with the anode and the cathode; and/or (d) a needle in fluid communication with the delivery fluid chamber. A needle may be configured, in some embodiments, to be in fluid communication with a delivery fluid chamber at one end and in fluid communication with a subject at the other. In some embodiments, electrodes may be configured to be renewed, for example, by making the cathode the anode and making the anode the cathode.

The present disclosure relates, according to some embodiments, to a prefilled electro-osmotic pump fluid reservoir comprising (a) a removable plug having a first plug surface, a second plug surface, and a pull-tab coupled to the first plug surface and the second plug surface; (b) a first, generally tubular fluid chamber having a first opening and at least one curvature having a concave edge, wherein the first plug surface is positioned to form a fluid-tight seal with the first opening of the first chamber; and/or (c) a second, generally tubular fluid chamber having a first opening and at least one curvature having a concave edge, wherein the second plug surface is positioned to form a fluid-tight seal with the first opening of the second chamber. A first fluid chamber may contain (e.g., be at least partially filled with) a first fluid (e.g., a pump fluid) and/or a second fluid chamber may contains (e.g., be at least partially filled with) a second fluid (e.g., a delivery fluid). In some embodiments, a delivery fluid may comprise at least one active pharmaceutical ingredient (e.g., a drug). In some embodiments, a prefilled electro-osmotic pump fluid reservoir may comprise (a) a first, generally tubular fluid chamber having a first opening and at least one curvature having a concave edge, wherein the first opening of the first chamber is (i) fluidly sealed by a first elastomeric septum and (ii) configured to removably engage at least a portion of an electro-osmotic pump; and/or (b) a second, generally tubular fluid chamber having a first opening and at least one curvature having a concave edge, wherein the first opening of the second chamber is (i) fluidly sealed by a second elastomeric septum (ii) configured to removably engage at least a portion of the electro-osmotic pump, wherein the first fluid chamber contains a first fluid and the second fluid chamber contains a second fluid.

BRIEF DESCRIPTION OF THE DRAWINGS

Some embodiments of the disclosure may be understood by referring, in part, to the present disclosure and the accompanying drawings, wherein:

FIG. 5F illustrates an elevation view of the reservoir system shown in FIG. 5B according to a specific example embodiment of the disclosure;

FIG. 5G is a sectional view of a reservoir system according to a specific example embodiment of the disclosure along section lines 5G-5G shown in FIG. 5F;

FIG. 5H is a sectional view of a reservoir system according to a specific example embodiment of the disclosure along section lines 5H-5H shown in FIG. 5F;

FIG. 5I illustrates a generally isometric view of the reservoir system shown in FIGS. 5B-5H;

DETAILED DESCRIPTION

Figure 1:
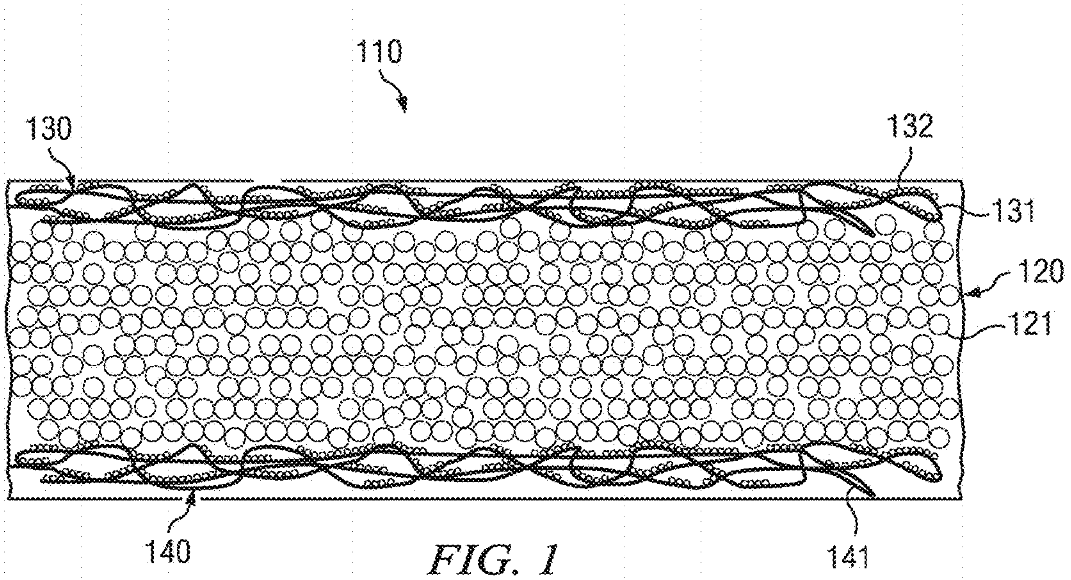
FIG. 1 illustrates a sectional view of the structure of a pump according to a specific example embodiment of the disclosure.

In some embodiments, the present disclosure relates, to a pump (e.g., an electro-osmotic pump). For example, a direct current (DC) electro-osmotic pump may comprise (i) a porous cathode optionally comprising a lanthanide oxide or actinide oxide (e.g., cerium oxide), (ii) a porous anode optionally comprising a lanthanide oxide or actinide oxide (e.g., cerium oxide), and (iii) a porous ceramic membrane between the cathode and the anode. In some embodiments, a porous cathode and/or a porous anode may be substantially metal free.

Lanthanide oxide or actinide oxide (e.g., cerium oxide) may be of mixed valence, for example in the case of cerium oxide it may comprise both $Ce^{4+}$ and $Ce^{3+}$. The oxide may also comprise hydrogen, for example as bound water or as bound $H^+$ or as bound $OH^-$, and it may also comprise bound oxygen, for example as bound $O_2$, bound superoxide radical anion $.O_2^-$, bound superoxide radical .OOH, or bound hydrogen peroxide $H_2O_2$. A pump may further comprise, in some embodiments, (a) an aqueous liquid to be pumped (e.g., in contact with the cathode, anode, and/or membrane), (b) a separator in fluid communication with the aqueous liquid to be pumped and/or (c) a second liquid (e.g., comprising a drug and/or an allergen) in fluid communication with the separator and separated from the aqueous fluid and configured and arranged such that movement of the aqueous liquid (e.g., by the action of the pump) moves the separator, which in turn moves the second liquid. In some embodiments, at least a part of the surface of the membrane may be in physical contact with the anode and/or at least a part of the opposite side of the membrane may be in physical contact with the cathode. A porous ceramic membrane may comprise, according to some embodiments, silica or ceria spheres from about 0.1 μm to about 10 μm in diameter (e.g., from about 0.5 μm in diameter to about 3 μm in diameter). In some embodiments, silica spheres may be selected from uncoated silica spheres, phosphosilicic-acid-coated silica spheres, borosilicic acid-coated silica spheres, and combinations thereof. A silica microsphere may optionally be microporous in some embodiments. A silica may comprise, according to some embodiments, metal ions (e.g., metal ions that may lower the glass transition temperature including, without limitation, calcium and/or sodium). For example, a silica may comprise a total concentration of sodium ions and calcium ions of less than about 10 mole percent.

In some embodiments, a porous ceramic membrane may be from about 0.1 mm to about 3 mm thick and/or from about 1 mm to about 30 mm wide. In some embodiments, an electro-osmotic pump may comprise a layered composition. According to some embodiments a layered composition may comprise: (i) a first layer comprising a porous substrate and a coating contacting at least a portion of the substrate; (ii) a second layer comprising a porous silica matrix; (iii) a third layer comprising a porous substrate and a coating contacting at least a portion of the substrate. In some embodiments, the coating may comprise a lanthanide oxide or actinide oxide (e.g., cerium oxide). In some embodiments, at least a portion of the first layer may be in contact with the second layer and at least a portion of the third layer may be in contact with the second layer. In some embodiments, a porous substrate of a composition layer may comprise carbon (e.g., non-woven carbon paper or cloth). A layered composition may comprise, in some embodiments, a coating with at least 2% by weight of cerium oxide, for example at least 5% by weight, or at least 10% by weight or at least 20% by weight or at least 30% by weight or at least 50% by weight cerium oxide. A layered composition may also comprise a perfluorosulfonic acid/polytetrafluoroethylene copolymer or a perfluorosulfonic acid/polytetrafluoroethylene copolymer).

The potential difference (V) between the anode and the cathode may be 0.1 volts$<V\leq3$ volts at about 25° C. and/or the flow rate per $cm^2$ of liquid-contacted area of the electro-osmotic pump may be at least 1 $\mu L\ min^{-1}\ cm^{-2}$, for example, at least 5 $\mu L\ min^{-1}\ cm^{-2}$, for example, at least 10 $\mu L\ min^{-1}\ cm^{-2}$, for example, at least 20 $\mu L\ min^{-1}\ cm^{-2}$ according to some embodiments. The flow rate of an electro-osmotic pump may vary, in some embodiments, about linearly (e.g., linearly) with applied current and/or applied voltage. According to some embodiments, the volume of liquid pumped may be monitored, for example, coulometrically monitored. An anode, a cathode, or both an anode and a cathode may comprise porous carbon (e.g., non-woven carbon, woven carbon paper, or cloth), in some embodiments. An anode may be and/or may comprise a carbon mesh according to some embodiments.

The present disclosure also relates, in some embodiments, to methods of producing a pump (e.g., an electro-osmotic pump). For example, a method may comprise adding an aqueous solution of $H_3PO_4$ and/or boric acid to a suspension of silica microspheres (e.g., from about 1 μm to about 3 μm in diameter), evaporating the water from the resulting suspension to form a powder, pressing the powder to form a pellet having at least two opposite surfaces, firing the pellet (e.g., for about 4 hours at from about 700° C. to about 900° C.) to form the ceramic membrane, and/or pressing two carbon paper electrodes (e.g., a cathode and an anode), each electrode optionally coated with a composition comprising cerium oxide nanocrystallites onto opposite surfaces of the ceramic membrane to form an electrode-membrane-electrode sandwich. In some embodiments, a method may further comprise washing and/or drying the ceramic membrane (e.g., after firing the pellet). A suspension of microspheres may comprise one of mono-disperse microspheres and poly-disperse microspheres according to some embodiments. A method may further comprise, in some embodiments, encapsulating the sandwich (e.g., encapsulating the sandwich in epoxy). According to some embodiments, the cathode and the anode may comprise carbon paper not coated with the conductive composition comprising cerium oxide nanoparticles. For example, a cathode and/or an anode may comprise carbon paper (e.g., plasma-treated carbon paper) without metal or substantially without metal.

The present disclosure also relates, in some embodiments, to methods of pumping a liquid (e.g., an aqueous liquid). For example, a method may comprise contacting the liquid with an electro-osmotic pump comprising (i) a cathode comprising carbon paper coated with a conductive composition comprising cerium oxide nanoparticles, (ii) an anode comprising carbon paper coated with a conductive composition comprising cerium oxide nanoparticles, and (iii) a ceramic membrane formed by fusing uncoated or phosphosilicic-acid-coated fused ceramic (e.g., silica) spheres (e.g., randomly packed between the cathode and the anode) and/or applying constant current to cause a potential difference between the anode and the cathode of from about 0.1 V to about 3 V such that the aqueous liquid is pumped. According to some embodiments, an aqueous liquid may be water (e.g., deionized water). A liquid (e.g., an aqueous liquid) may comprise water containing a total solute (e.g., electrolyte) concentration of less than about 50 mM, less than about 10 mM, less than about 5 mM, less than about 1 mM, less than about 0.1 mM. A pump may further comprise, in some embodiments, a separator (e.g., a fluid separator comprising air and/or an oil) in fluid communication with an aqueous liquid to be pumped and a second liquid in fluid communication with the separator and separated from the aqueous fluid. A method may further comprise moving the aqueous liquid such that the separator moves, which in turn moves the second liquid. A second liquid may comprise, for example, a drug (e.g., insulin, an antibiotic, and/or a biologic drug) and/or an allergen. In some embodiments, applying current comprises applying a current, such that the current density, based on the water-contacted, geometrical area of the electrodes is from about 0.01 $mA\ cm^{-2}$ to about 2 $mA\ cm^{-2}$. The flow rate may vary, in some embodiments, about linearly (e.g., linearly) with applied current and/or applied voltage. For example, the flow rate of an aqueous liquid may vary about linearly (e.g., linearly) with applied current density from about 10 $mL\ min^{-1}\ A^{-1}\ cm^{-2}$ to about 700 $mL\ min^{-1}\ A^{-1}\ cm^{-2}$. At any instant, the flow rate of the aqueous liquid per unit cross sectional aqueous liquid contacted area may be, in some embodiments, between about 10 $\mu L\ min^{-1}\ cm^{-2}$ and about 100 $\mu L\ min^{-1}\ cm^{-2}$. In some embodiments, applying constant current may produce substantially no bubbles (e.g., no bubbles comprising hydrogen and/or oxygen). Application of constant current may comprise applying, according to some embodiments, two or more pulses. For example, in some embodiments the pulses may occur at an interval of less than 10 minutes, 5 minutes, 2 minutes, 1 minute, and/or 30 seconds.

According to some embodiments, a method of pumping a liquid (e.g., aqueous liquid) may comprise contacting the liquid with an electro-osmotic pump comprising (i) a cathode comprising carbon paper coated with a conductive composition comprising cerium oxide nanoparticles, (ii) an anode comprising carbon paper coated with a conductive composition comprising cerium oxide nanoparticles, and (iii) a ceramic membrane formed for example by fusing uncoated or phosphosilicic-acid-coated fused ceramic (e.g., silica) spheres (e.g., randomly packed between the cathode and the anode) and/or applying a constant potential difference or voltage between the anode and the cathode of from about 0.1 V to about 3 V such that the aqueous liquid is pumped. According to some embodiments, an aqueous liquid may be water (e.g., deionized water). A liquid (e.g., an aqueous liquid) may comprise a solute at a concentration of less than about $10^{-2}$ moles per liter in some embodiments. A pump may further comprise, in some embodiments, a separator (e.g., a fluid separator comprising air and/or an oil) in fluid communication with an aqueous liquid to be pumped and a second liquid in fluid communication with the separator and separated from the aqueous fluid. A method may further comprise moving the aqueous liquid such that the separator moves, which in turn moves the second liquid. A second liquid may comprise, for example, a drug (e.g., insulin, an antibiotic, and/or a biologic drug) and/or an allergen. In some embodiments a voltage from about 0.01 V to about 3 V, preferably from about 0.02 V and about 2 V, for example between 0.5 V and 1.2 V is applied. In some embodiments, applying constant potential difference or voltage may produce substantially no bubbles (e.g., no bubbles comprising hydrogen and/or oxygen). Application of constant current may comprise applying, according to some embodiments, two or more pulses. For example, in some embodiments the pulses may occur at an interval of less than 10 minutes, 5 minutes, 2 minutes, 1 minute, and/or 30 seconds.

The present disclosure also relates, in some embodiments, to a device delivering fluids (e.g., solutions of drugs). For example, a device may comprise a reservoir, a controller and one or more sensors. According to some embodiments, an electro-osmotic pump fluid reservoir may comprise two generally tubular fluid chambers from about 2 mm to about 10 mm in inside diameter. According to some embodiments, the interior surface of first, second or both of the fluid chambers may comprise a hydrophobic coating. In some embodiments, the two generally tubular fluid chambers may comprise a first opening and at least one curvature having a concave edge. According to some embodiments, the first opening of the first fluid chamber may face and be spaced apart from the first opening of the second fluid chamber. In some embodiments, an electro-osmotic pump fluid reservoir may comprise at least one curvature having a concave edge of the second fluid chamber that may be coplanar with and proximal to the concave edge of the curvature of the first fluid chamber. In some embodiments, the first fluid chamber may be substantially in a first plane and the second fluid chamber may be substantially in a second plane. In some embodiments, the first plane and second plane may be substantially parallel to each other and the first fluid chamber may be substantially overlaying the second fluid chamber. According to some embodiments, the volume in the first chamber may be smaller, greater or the same as the volume in the second chamber. In some embodiments, a concave edge of the at least one curvature of the first fluid chamber and the concave edge of the at least one curvature of the second fluid chamber of an electro-osmotic pump fluid reservoir may partially define a well configured to receive a controller assembly.

According to some embodiments, a first generally tubular fluid chamber of an electro-osmotic pump fluid reservoir may comprise one or more additional curvatures oriented in substantially the same plane as and concentrically with the first curvature and additional curvatures of the first fluid chamber, and one or more hairpin turns positioned between and in fluid communication with the curvatures of the first fluid chamber. In some embodiments, second generally tubular fluid chamber of an electro-osmotic pump fluid reservoir may comprise one or more additional curvatures oriented in substantially the same plane as and concentrically with the first curvature of the second fluid chamber, and one or more hairpin turns positioned between and in fluid communication with the curvatures of the second fluid chamber. According to some embodiments, an electro-osmotic pump fluid reservoir may comprise two generally tubular fluid chambers with a chamber volume of from about 0.2 mL to about 5 mL. The present disclosure also relates to an electro-osmotic fluid delivery system. In some embodiments, an electro-osmotic fluid delivery system may comprise an electro-osmotic pump, an electro-osmotic pump reservoir, a removable controller assembly and a cannula and/or a needle in fluid communication with a delivery fluid chamber. According to some embodiments an electro-osmotic pump may comprise (i) a porous cathode coated with a conductive composition comprising cerium oxide nanoparticles, (ii) a porous anode coated with a conductive composition comprising cerium oxide nanoparticles, and (iii) a porous ceramic membrane between the cathode and the anode. In some embodiments, an electro-osmotic pump reservoir may comprise a pump fluid chamber in fluid communication with the electro-osmotic pump and a delivery fluid chamber in fluid communication with the electro-osmotic pump. In some embodiments, a removable controller assembly may be in electrical communication with the anode and the cathode. In some embodiments an electro-osmotic fluid delivery system may comprise a pump fluid chamber comprising pump fluid proximal to a pump. In some embodiments, the delivery fluid chamber may comprise pump fluid proximal to an electro-osmotic pump, a delivery fluid distal to the electro-osmotic pump and proximal to a needle, and a separator positioned between the pump fluid and the delivery fluid. In some embodiments, an electro-osmotic fluid delivery system may comprise pump fluid consisting essentially of water and a delivery fluid may comprise a pharmaceutically active ingredient, an allergen, an antibody, and/or a nutrient. In some embodiments, an electro-osmotic fluid delivery system may comprise a removable controller assembly comprising a user interface, a processor, memory in electrical signal communication with the processor, and a power source in electrical communication with the processor, and/or the memory. According to some embodiments, an electro-osmotic fluid delivery system controller assembly may comprise a user interface configured to permit the magnitude and/or duration of the current to be applied to a pump, the magnitude and/or duration of the potential difference or voltage to be applied to a pump, or both to be set and/or changed by a user. In some embodiments, a user interface may comprise at least one input key. According to some embodiments, an electro-osmotic fluid delivery system may further comprise a transmitter and/or receiver in signal communication with a controller, a pump, or a controller and a pump. In some embodiments, an electro-osmotic fluid delivery system may comprise an adhesive pad and/or an elastic band fixed to the reservoir. According to some embodiments, an electro-osmotic fluid delivery system may comprise a pump fluid chamber comprising an outer pump fluid chamber curvature comprising a concave edge, an inner pump fluid chamber curvature having a concave edge concentric to and coplanar with the concave edge of the outer pump fluid chamber curvature, and a hairpin turn in fluid communication with the outer and inner pump fluid chamber curvatures. In some embodiments, the delivery fluid chamber may comprise an outer delivery fluid chamber curvature having a concave edge, an inner delivery fluid chamber curvature having a concave edge concentric to and coplanar with the concave edge of the outer delivery fluid chamber curvature, and a hairpin turn in fluid communication with the outer and inner delivery fluid chamber curvatures. According to some embodiments, a pump fluid chamber and a delivery fluid chamber at least partially encircle a removable controller assembly.

The present disclosure also relates to a method of delivering a fluid to a subject. For example, a method may comprise (i) providing an electro-osmotic drug delivery system comprising a reservoir, a removable controller and a needle and/or a cannula in fluid communication with the delivery fluid chamber, (ii) inserting the needle and/or cannula into a subject; and (iii) applying a constant potential difference or constant current between the anode and cathode.

In some embodiments, an electro-osmotic pump may comprise (i) a porous cathode coated with a conductive composition comprising cerium oxide nanoparticles, (ii) a porous anode coated with a conductive composition comprising cerium oxide nanoparticles, and (iii) a porous ceramic membrane between and in at physical contact with the cathode and the anode. In some embodiments, an electro-osmotic reservoir may comprise a pump fluid chamber and a delivery fluid chamber in fluid communication with the electro-osmotic pump. In some embodiments, a pump fluid chamber may comprise a first aliquot of pump fluid proximal to the electro-osmotic pump. In some embodiments, a delivery fluid chamber may comprise a second aliquot of pump fluid proximal to a pump, a delivery fluid positioned distal to the electro-osmotic pump, and a separator positioned between the second aliquot of pump fluid and the delivery fluid. In some embodiments, a removable controller may be in electrical communication with an anode and a cathode. In some embodiments, application of a constant potential difference or a constant voltage may comprise moving a volume of a first aliquot of pump fluid from a pump fluid chamber across a porous membrane to a delivery fluid chamber to commensurately increase the volume of the second aliquot of pump fluid in the delivery fluid chamber and through a needle and/or cannula into a subject. In some embodiments, the volume of delivery fluid passing through a needle into a subject may be substantially the same as the increased volume of the second aliquot of pump fluid in the delivery fluid chamber. In some embodiments, a pump fluid may consist essentially of deionized water. In some embodiments, a delivery fluid may comprise insulin, an antibiotic, a biologic drug, and/or allergen. According to some embodiments, the flow rate of a pump fluid may vary linearly with voltage. At any instant the flow rate of a pump fluid per unit cross sectional pump fluid-contacted area may be between about 1 $\mu L\ min^{-1}\ cm^{-2}$ and about 1 $mL\ min^{-1}\ cm^{-2}$, for example, between about 10 $\mu L\ min^{-1}\ cm^{-2}$ and about 100 $\mu L\ min^{-1}\ cm^{-2}$. Applying constant potential difference or constant voltage may produce substantially no bubbles according to some embodiments.

The present disclosure relates, in some embodiments, to methods, devices, and systems for delivering a composition (e.g., a fluid composition) to a subject (e.g., human and/or non-human animal). For example, delivering a composition (e.g., a fluid composition) to a subject may comprise subcutaneous or other in-tissue delivering (e.g., pumping) of dissolved or solution-dispersed therapeutic drugs. Some pumps of the present disclosure may be of the type that deliver insulin stored in a remote reservoir fluidically connected (e.g., by tubing) to a cannula. Delivery may be accomplished by putting a pump in fluid communication with one or more tissues in a subject. For example, a pump may be in a system that is skin mounted or attached with its cannula connected by a short tubing. In some embodiments, the volume of the unit may be smaller than about 15 $cm^3$, for example, smaller than about 10 $cm^3$, and for example, smaller than about 5 $cm^3$. In some embodiments of the present disclosure, the reservoir may contain a sufficient volume of a fluid (e.g., drug solution or dispersion) for delivery over about a 1-10-day period (e.g., about a 2-3 day period).

Pump Membranes

According to some embodiments a pump may comprise a membrane (e.g., a porous membrane) and two or more electrodes. For example, a pump may be configured as an electro-osmotic pump and comprise a membrane (e.g., a porous membrane), a cathode at least a portion of which is in contact with the membrane, and an anode at least a portion of which is in contact with the membrane. A membrane (e.g., a porous membrane) may have any desired or required shape and/or size. According to some embodiments, a membrane (e.g., a porous membrane) may have a generally circular shape with a circumference and two opposing surfaces. A membrane (e.g., a porous membrane) may have a diameter less than, 8 mm, for example less than 6 mm, for example less than 1.3 mm. A membrane may have a thickness less than 3 mm, for example less than 2 mm, for example, less than 1.3 mm. The porous membrane can be ceramic; it may comprise, for example silica or ceria. A membrane (e.g., a porous membrane) may comprise, for example, mono-disperse or polydisperse silica microparticles with diameters of less than about 10 μm, for example, less than about 10 μm, for example, less than about 5 μm, for example, less than about 2 μm, for example, less than about 1 μm, for example, less than about 0.5 μm, for example, less than about 0.2 μm.

A membrane (e.g., a porous membrane) may comprise, in some embodiments, a porous ceramic or a polymeric organic material having anionic or cationic functions. A membrane may have a polyanionic surface. Examples of useful porous ceramic materials include silica, ceria, cerium phosphate, zirconia, titania, alumina, zirconium phosphate, zirconium silicate, phosphosilicate glass, borosilicate glass. Optionally, a membrane may be formed by heating microspheres of a ceramic, for example, heating fused silica microspheres with phosphoric or polyphosphoric acid. Examples of polymeric-organic membranes include cation exchangers like NAFION® (a perfluorosulfonic acid/polytetrafluoroethylene copolymer), sulfonated polystyrene and its co-polymers.

In some embodiments, a membrane may be formed by pelletizing at 300 psi then firing phosphosilicic acid coated 1 μm mono-disperse silica microspheres at 700° C. for 4 h. A membrane may be sandwiched between an anode and a cathode, each of which is coated with a conductive composition comprising cerium oxide nanoparticles. According to some embodiments, a membrane may be made of porous silica that has an optional phosphosilicic acid and/or borosilicic acid shell. Optionally, a silica may be microporous. A microporous silica may have pores with a diameter of, for example, less than about 5 μm or less than about 100 nm. A silica may, in some embodiments, comprise a metal oxide (e.g., $Na_2O$, CaO). For example, a silica may comprise a mole percent of $Na_2O$, CaO, or $Na_2O$+CaO of from about 1 mole percent to about 5 mole percent, from about 5 mole percent to about 10 mole percent, and/or from about 10 mole percent to about 20 mole percent. A membrane may be formed, according to some embodiments, by fusing a phosphosilicic acid coating or a borosilicic acid coating onto fused silica spheres of 1 μm diameter. In some embodiments, a membrane may comprise ceria ($CeO_2$) or zirconia ($ZrO_2$) reacted with a phosphorus and oxygen containing compound, such as phosphoric acid or a polyphosphoric acid or phosphorus pentoxide, optionally to form a phosphated ceria or zirconia surface, such as a $Ce_3(PO_4)_4$ or Zr3$(PO_4)_4$ enriched surface. The zirconia may be stabilized, for example, with yttria, calcium ("calcia"), or other suitable stabilizers. A membrane may comprise, according to some embodiments, alumina ($Al_2O_3$) reacted with a phosphorus and oxygen containing compound, such as phosphoric acid or a polyphosphoric acid or phosphorus pentoxide, optionally to form a phosphated alumina surface. In some embodiments, a membrane may comprise glass, such as soda lime glass or borosilicate glass or lead glass, reacted with a phosphorus and oxygen containing compound, such as phosphoric acid or a polyphosphoric acid or phosphorus pentoxide, optionally to form a phosphated glass surface. In some embodiments, a membrane may comprise a polyvinyl phosphonate polymer or co-polymer membranes, which may be made water-insoluble by crosslinking or according to other known methods.

In some embodiments, a porous membrane may comprise vitreous and/or crystalline ceramics, or mixed vitreous and crystalline oxides comprising, at least in their water or other fluid contacting surface, phosphorus (e.g., in the five-valent oxidation state) and/or boron (e.g., in the five-valent oxidation state). Examples of membrane materials include phosphosilicic acid and/or phosphosilicate glass on fused silica; borosilicic acid on fused silica; zirconia ($ZrO_2$) or ceria ($CeO_2$) reacted with a phosphorus and oxygen containing compound, such as phosphoric acid or a polyphosphoric acid or phosphorus pentoxide, optionally to form a phosphated zirconia surface, such as a $Zr_3(PO_4)_4$ or $Ce_3(PO_4)_4$ enriched surface, with the zirconia optionally phase-stabilized, for example, with yttria or with calcium oxide; or alumina ($Al_2O_3$) reacted with a phosphorus and oxygen containing compound, such as phosphoric acid or a polyphosphoric acid or phosphorus pentoxide, optionally to form a phosphated alumina surface; or a glass, such as soda lime glass, or a borosilicate glass or a lead glass, reacted with a phosphorus and oxygen containing compound, such as phosphoric acid or a polyphosphoric acid or phosphorus pentoxide, optionally to form a phosphated glass surface. A phosphosilicate glass and/or a borosilicate glass may be used, the surface of which may be optionally phosphorous-oxide enriched and/or boron oxide enriched. Porous metal phosphates such as $AlPO_4$, $Zr_3(PO_4)_4$, $Ce_3(PO_4)_4$, $Zn_3(PO_4)_4$ or $FePO_4$ or $Fe_3(PO_4)_2$ may be used in some embodiments. Packing of fused spheres, according to some embodiments, may be random, haphazard, and/or incompletely ordered.

According to some embodiments, a microsphere may have a diameter (e.g., an average diameter) of less than about 10 μm (e.g., less than about 10 μm, less than about 5 μm, less than about 2 μm, less than about 1 μm, less than about 0.5 μm, less than about 0.2 μm, and/or less than about 0.1 μm).

In accordance with exemplary embodiments and to remove any unbound phosphoric acid resulting from the above process, the about 0.8 cm outer diameter ceramic membranes may be washed with copious amounts of water. After assembly of the membranes in the sandwiches shown in FIG. 5, they may be washed again for about 25 min at about 10 $\mu L\ min^{-1}$ flow rate. The washing-water may come from a commercially-available syringe pump or other suitable apparatus.

Pump Electrodes

A potential difference (i.e., a voltage) and/or a current may be applied across the membrane through electrically conductive materials (e.g., electrodes) positioned on opposite sides. The composition of electrically conductive materials may be selected such that the application of a potential difference results in a reaction by which $H^+$ and/or $OH^-$ move across and/or through a membrane according to some embodiments. For example, it may be desirable to select a composition such that protons ($H^+$) move across and/or through a membrane. Electrodes, (e.g., the anode and cathode), according to some embodiments, may be porous. In some embodiments an anode may comprise carbon, for example, woven or non-woven carbon cloth or paper, or carbon foam. One example of a carbon cloth electrode is TGP-H-030, made by Toray Industries Inc., 2-1, Nihonbashi-Muromachi 2 Chome, Chuo-ku, Tokyo, Japan. A porous carbon anode may be coated (e.g., advantageously coated) with, for example, colloidal tin oxide, sold, for example, as a NYACOL® SN15 dispersion by Nyacol Nano Technologies Inc., Ashland, Mass. For example, an anode may be, for example, dip-coated, and/or spray-coated with a NYACOL® SN15 dispersion. In some embodiments, an anode may be coated with a ceria sol, for example, colloidal ceria, sold by NYACOL® Nano Technologies Inc., Ashland, Mass., either with nitrate counter-ions or with acetate counter-ions, the ceria particle sizes being in the sol according to the manufacturer 10-20 nM. A carbon electrode may be first coated with colloidal tin oxide, then with colloidal ceria, according to some embodiments.

In some embodiments, a porous cathode may be carbon-based. For example, a cathode may be woven or non-woven carbon cloth or paper, or carbon foam. A carbon-based, porous cathode, according to some embodiments, may be made hydrophilic. For example, it may be desirable or necessary to make a carbon-based, porous cathode (e.g., a woven or non-woven carbon cloth or paper or a carbon foam) hydrophilic by exposure to a plasma (e.g., an about 20 torr oxygen plasma for about an hour).

According to some embodiments, it may be desirable, preferred, and/or required to use electrodes comprising a conductive composition comprising cerium oxide nanoparticles. An electrode may comprise enough of a conductive composition comprising cerium oxide nanoparticles to have a coulombic capacity of at least 2 millicoulombs (mC), at least 10mC, at least 20 mC, at 100 mC, at least 0.2 C, at least 0.5 C; or at least 1 C. In some embodiments, the conductivity of the cerium oxide nanocrystallytes comprising coatings of the electrodes can be increased by incorporating carbon in the coatings.

Each electrode may independently comprise a plasma-treated carbon paper with or without a metallic conductive material, according to some embodiments. For example, it may be desirable and/or required to use electrodes that do not include cerium oxide nanoparticles. In some embodiments, electrodes (e.g., a cathode, an anode, or both a cathode and an anode) may be substantially free (e.g., free) of metal. Non-metallic conductive materials may confer electrode operability, according to some embodiments. Non-metallic conductive materials may comprise, for example, carbon, carbon paper, woven carbon paper, non-woven carbon paper, plasma-treated carbon paper, carbon fiber, polyacetylene, polypyrrole, and polyaniline, and combinations thereof. In some embodiments, a pump may comprise a porous, substantially metal-free anode comprising plasma-treated carbon paper and a porous, substantially metal-free cathode comprising plasma-treated carbon paper. Without limiting any embodiment to any specific mechanism of action, plasma treatment may form electrooxidizable and/or electroreducable groups on carbon surfaces. For example, plasma treatment may produce a carbon surface comprising one or more conjugated groups. Conjugated groups may include one or more phenols (e.g., diphenols) and/or one or more carbonyls (e.g., quinones).

Substantially metal-free electrodes and/or substantially silver-free electrodes comprising cerium oxide may provide durability, stability of flow-rate, reproducibility of flow-rate, controllability of flow, and/or combinations thereof. In some embodiments, an electrode may be substantially free of a metal (e.g., a specific metal, specific metals, or all metals) even if it contains a trace of the metal (e.g., an amount insufficient to alone support electro-osmotic flow).

The desired porosity of an electrode may be achieved, for example, by using a porous substrate (e.g., a porous, conductive, and optionally non-corroding substrate), that need not be electrochemically reactive. Some useful electrode materials, according to some embodiments, include forms of porous carbon for example woven or non-woven carbon cloth or carbon paper or gold mesh or silver mesh. Anodes may generate, in some embodiments, protons in their operation. According to some embodiments, cathodes may generate in their reaction hydroxide anions and/or may consume protons in their operations.

An electrode may have any desired or required shape and/or size. According to some embodiments, an electrode (e.g., a porous electrode) may have a generally circular shape with a circumference and two opposing surfaces. In some embodiments, an electrode (e.g., a porous electrode) may have a similar or the same size and shape as its adjacent membrane. An electrode (e.g., a porous electrode) may have a diameter less than about 8 mm, less than about 6 mm, and/or less than about 1.3 mm. An electrode (e.g., a porous electrode) may have a diameter about 5 cm or less, about 2 cm or less, about 1 cm or less, and/or about 6 mm or less. An electrode (e.g., a porous electrode) may have a thickness less than about 3 mm, for example less than about 2 mm, for example, less than about 1.3 mm. In some embodiments, the outer diameter of an electrode-membrane-electrode sandwich may be less than about 5 cm and more than about 0.1 cm; for example, less than about 3 cm and more than about 0.3 cm; for example, less than 1 cm and more than 0.4 cm.

In some embodiments, electrodes may be formed of materials that satisfy the following conditions: (1) non-gassing electrode reactions (e.g., no hydrogen evolved at cathode and no oxygen evolved at anode); and/or (2) anode reaction generates protons and/or metal cations and cathode reaction consumes protons and/or metal cations.

According to some embodiments, DC electro-osmotic pumps with anodes that do not evolve gaseous oxygen and/or cathodes that do not evolve gaseous hydrogen may be desired and/or preferred. Anodes (e.g., preferred anodes) may generate, in some embodiments, protons and/or metal cations in their operation. In some embodiments, anodes may generate protons and/or metal cations in their operation. According to some embodiments, cathodes may generate in their reaction hydroxide anions and/or may consume protons and/or metal cations in their operations.

Pumps

In some embodiments components of a pump may be simple and inexpensive. In some embodiments, total cost of pump components may be less than $2.00, for example $1.00 (in 2011 USD). Components of a pump may comprise, a pair of PVC receptacles, a pair of contact strips (e.g., thin gold foil or nickel) a pair of coated carbon paper electrodes, a ceramic membrane, and silicon tubing. The components of a pump may be assembled by sandwiching a membrane between electrodes. In some embodiments, the diameter of the membrane and electrodes is 8 mm. In some embodiments, the covered rim is less than about 0.3 cm and more than about 0.03 cm, for example, greater than about 0.05 cm and less than about 0.2 cm; the water exposed area may be about 25 $cm^2$ or less, for example, about 10 $cm^2$ or less, for example, about 4 $cm^2$ or less, for example, about 1 $cm^2$ or less, for example, 0.5 $cm^2$ or less, for example, about 0.3 $cm^2$ or less, for example, about 0.1 $cm^2$ or less, for example, about 0.05 $cm^2$ or less. After assembly of the membranes in the sandwiches, they may be washed again for about 25 min at about 10 $\mu L\ min^{-1}$ flow rate. The washing-water may come from a commercially-available syringe pump or other suitable apparatus.

In some embodiments an electrode may be in close physical contact with the membrane, meaning that there is little or no aqueous liquid (e.g., free-flowing aqueous liquid) separating either electrode from the membrane. In some embodiments, means for good physical contact may include an electrochemically non-reactive thin film (e.g., a thin film of an electron and/or hole conductor) deposited on both sides of the membrane. A non-reactive conductive film may comprise, for example, carbon or gold. The film may be preferably thin enough to be porous in some embodiments. The film may be deposited, for example, by sputtering or evaporation or it could be painted or sprayed. Available carbon pastes such as SPI carbon #5065 or carbons available from Timcal, Westlake Ohio, such as Timcal Super P carbons may be used. In some embodiments, physical contact may be improved by polishing flat a ceramic membrane before pressing onto it the electrochemically reactive component containing carbon paper electrodes. In some embodiments, carbon paper may be hot-pressed onto the two sides of a ceramic membrane at a temperature typically exceeding about 500° C., for example, exceeding about 600° C., for example, exceeding about 700° C., for example, exceeding about 800° C., for example, exceeding about 900° C., for example, exceeding about 1000° C., at a pressure typically exceeding about 0.1 MPa, for example, exceeding about 0.2 MPa, for example, exceeding about 0.5 MPa, for example, exceeding about 1.0 MPa, for example, exceeding about 2 MPa.

In some embodiments, the membrane could be dipped in a solution containing a gold complex like $AuCl_4^-$ or $Au(CN)_2$ of which gold or platinum could be precipitated by a reductant such as a reductant used in electroless plating of gold. In some embodiments, examples of reductants include borohydrides and hypophosphites. In some embodiments, a ceramic membrane may be coated by an electrode-forming paste on its two sides. According to some embodiments, a compartment containing a pump fluid (e.g., pumped water or aqueous solution), and also a compartment containing a delivery fluid (e.g., a drug solution or suspension) may be made, for example, by molding a plastic. Either or both compartments may have a port or septum, such as a septum made of an elastomer, to allow their filling with water or aqueous solution or with a drug solution or suspension. Filling could be done, for example, with a syringe. Either or both compartments may have a hydrophobic vent allowing air or other gases to escape, for example during filling. A vent may optionally comprise a hydrophobic porous material, to allow the escape of gases without allowing leakage of the water or aqueous solution or of the drug suspension or solution. Examples of hydrophobic porous vent materials include but are not limited to hydrophobic gas diffusion membranes optionally made of woven and non-woven fibrous perfluorinated polymers, exemplified by materials used in zinc air batteries, such as the Excellerator™ PTFE Gas Diffusion Membrane of W. L. Gore & Associates of Newark, Del.

Optionally, a drug-containing compartment may contain a drug concentrate in a non-aqueous solution or dispersion, or a solid comprising the drug (e.g., for longer shelf life). In this case the drug solution or suspension is prepared prior to use, for example by adding water or an aqueous solution to the drug containing compartment prior to use. This may be preferred, for example, when the delivered drug is glucagon, available from Eli Lilly & Co. Indianapolis, Ind., because the shelf life of its typically injected solution is usually only of about a day.

In some embodiments, a nanocrystalline cerium oxide comprising anode and a cathode may be reversible and identical except for their local pH difference. Little, if any, oxygen may be evolved for example if $Ce^{3+}$ is electrooxidized to $Ce^{4+}$ at the anode, and no hydrogen is evolved if, for example, $Ce^{4+}$ is electroreduced to $Ce^{3+}$ at the cathode, or, for example, if cerium oxide bound oxygen is electroreduced at the cathode and is electro-generated at the anode.

FIG. 1 illustrates a sectional view of the structure of pump 110 according to a specific example embodiment of the disclosure. Pump 110 comprises a $SiO_2$ membrane 120, comprising silica spheres 121, sandwiched between electrodes 130 and 140. Electrodes 130 and 140 each comprise a carbon paper substrate (131 and 141, respectively) covered with the coating comprising cerium oxide nanocrystallites and optionally also carbon and/or Nafion 132. In some embodiments, electrodes 130 and 140 may each comprise a carbon paper substrate (131 and 141, respectively) that are not covered with the coating comprising cerium oxide nanocrystallites, but are substantially metal free. The 1.3 mm thick 8 mm diameter membrane may be formed by fusing phosphosilicic acid coated silica microspheres. Flow-through anode 130 and cathode 140 may be 280 μm thick 78% porosity carbon paper coated with the composition comprising cerium oxide nanocrystallites.

Figure 2:
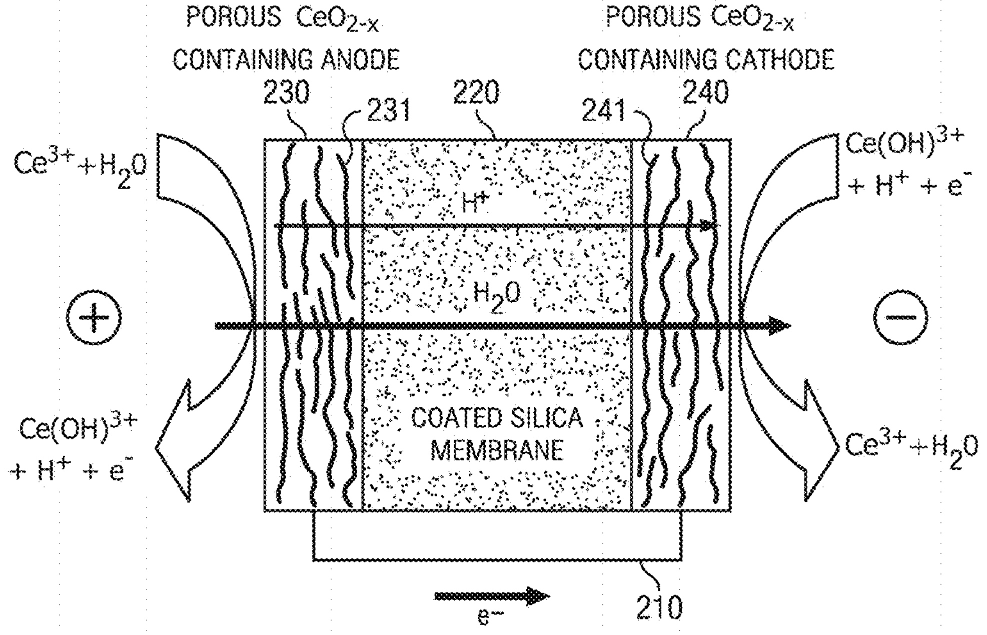
FIG. 2 illustrates a sectional view of a pump with electrode reactions and transport processes according to a specific example embodiment of the disclosure.

FIG. 2 illustrates a sectional view of pump 210, with example electrode reactions, and transport processes according to a specific example embodiment of the disclosure. One or more other (e.g., alternate) reactions may take place, according to some embodiments, including, for example, reactions involving $O_2$ bound to ceria, superoxide bound to ceria, and/or hydrogen perozide. Pump 210 includes a pair of identical, porous cerium oxide (i.e., $CeO_{2-x}$) electrodes 230 and 240, each of which comprises a carbon paper substrate (231 and 241, respectively) covered with a coating comprising a cerium oxide (232 and 242, respectively), sandwiching ceramic membrane 220. In some embodiments, electrodes 230 and 240 may include carbon paper substrates 231 and 241, respectively, but exclude cerium oxide coatings. The electrochemically reactive component of porous anode 230 or cathode 240 may be applied by any method. FIG. 2 illustrates that application of current (or voltage) across the anode 230 and cathode 240 may drive protons, produced in the anodic reaction $Ce^{3+}+H_2O \rightarrow Ce(OH)^{3+}+H^++e^-$, to the cathode, where they are consumed by the cathodic reaction $Ce(OH)^{3+}+H^++e^- \rightarrow Ce^{3+}+H_2O$, the $H_2O$ optionally hydrating the $Ce^{3+}$ ions.

Figure 3A:
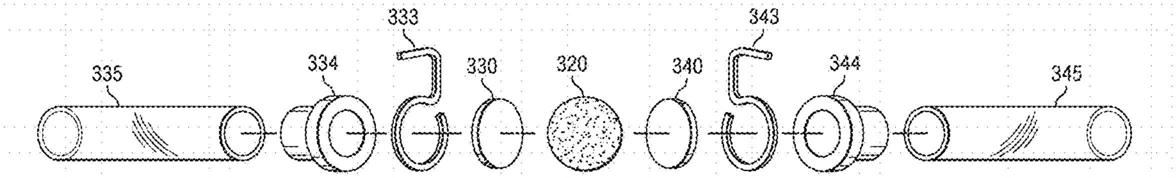
FIG. 3A illustrates an exploded view of the pump shown in FIG. 3B according to a specific example embodiment of the disclosure.

FIG. 3A illustrates an exploded view of a pump according to a specific example embodiment of the disclosure. FIG. 3A depicts the low-cost components of a pump. From left to right, the components are: silicon tubing 335, PVC frame 334, gold strip 333, carbon paper anode 330 coated with a composition comprising cerium oxide nanocrystallites, ceramic membrane 320, carbon paper cathode 340 coated with a composition comprising cerium oxide nanocrystallites, gold strip 343, PVC Frame 344, silicon tubing 345. The estimated cost of the depicted pump is $1.00 (in 2011 USD).

Figure 3B:
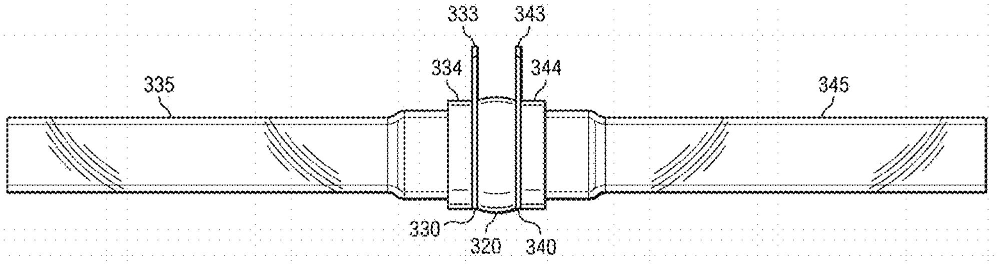
FIG. 3B illustrates an assembled pump according to a specific example embodiment of the disclosure.

FIG. 3B illustrates an assembled pump according to a specific example embodiment of the disclosure. From left to right, the components are: silicon tubing 335, PVC frame 334, gold strip 333, carbon paper anode 330 coated with a composition comprising cerium oxide nanocrystallites, ceramic membrane 320, carbon paper cathode 340 coated with a composition comprising cerium oxide nanocrystallites, gold strip 343, PVC frame 344, silicon tubing 345. The sandwiches may be encapsulated in an epoxy, with foil lips (e.g., gold foil lips) (333, 343) inserted between the membrane 320 and the electrodes 330, 340 for electrical contacting. An assembled electrode-membrane-electrode sandwich may be washed with water from a syringe pump (e.g., Cole Parmer 780100C, Vernon Hills, Ill.) for 25 min at 10 μL $min^{-1}$ flow rate before use.

Reservoirs

An assembled pump may be inserted into a gap of a reservoir assembly. According to some embodiments, a reservoir assembly may comprise two compartments. In some embodiments, one compartment may contain pumped water or aqueous solution, and a second compartment may contain a drug solution or of a solution containing multiple drugs, stored in a reservoir suspension. In some embodiments, a reservoir may be made, for example, by molding a plastic. In some embodiments, either or both compartments may have a port or septum, such as a septum made of an elastomer, to allow their filling with the water or aqueous solution or with the drug solution or suspension. According to some embodiments, a reservoir assembly may have any desirable geometric configuration. Similarly, fluid chambers in a reservoir assembly may have, in some embodiments, any desired configuration. A reservoir assembly, for example, may have an annular shape. In some embodiments, an annular reservoir assembly may comprise a gap (e.g., for insertion of a pump) occupying a portion (e.g., less than about 20%, less than about 10%, less than about 5%, and/or less than about 3%) of the annular circumference. A reservoir assembly may be filled, for example, with a syringe. In some embodiments, either or both compartments may also have a hydrophobic vent allowing air or other gases to escape, for example during loading and/or operation. A vent may optionally comprise a hydrophobic porous material, to allow the escape of gases without allowing leakage of the water or aqueous solution or of a drug suspension or solution. Examples of hydrophobic porous vent materials include, but are not limited to, hydrophobic gas diffusion membranes optionally made of woven and non-woven fibrous perfluorinated polymers, exemplified by materials used in zinc air batteries, such as the Excellerator™ PTFE Gas Diffusion Membrane of W. L. Gore & Associates of Newark, Del. Venting air and/or other gases may reduce and/or prevent an undesirable pressure change in one or more chambers according to some embodiments. For example, heat (e.g., body heat, sunlight, and/or others) may lead to an increase in pressure that, if unchecked, may lead to an unplanned change in flow rate. This, in turn, may lead to over-dosing or under-dosing of a drug or other material in a delivery fluid.

One or more reservoir surfaces (e.g., surfaces that contact a pump fluid, a separator, and/or a delivery fluid) may be hydrophobic according to some embodiments. For example, a reservoir surface may be hydrophobic due to its intrinsic composition, chemical treatment, and/or application of a hydrophobic coating (e.g., a long-chain alkyl trialkoxysilane).

In some embodiments, a delivery fluid-containing compartment may contain an active pharmaceutical ingredient (e.g., a drug) concentrate in a non-aqueous solution or dispersion, or a solid comprising the active pharmaceutical ingredient (e.g., for longer shelf life). In some embodiments, an active pharmaceutical ingredient solution or suspension may be prepared prior to use, for example by adding water or an aqueous solution to the drug containing compartment prior to use. This may be desirable, for example, when the delivered active pharmaceutical ingredient is glucagon, available from Eli Lilly & Co. Indianapolis, Ind., because the shelf life of its typically injected solution is usually only about a day.

According to some embodiments, a pump may comprise means for metering (e.g., accurately metering) a fluid, means for pumping a fluid, and/or an implanted cannula. An implanted cannula may be connected, for example, through plastic tubing to a flow-causing pump, which pumps or delivers a defined volume of a drug containing solution, or of a solution containing multiple drugs, stored in a reservoir. In some embodiments, drug reservoir volumes may be varied by increasing the thickness and/or length of the reservoir. It may be desirable to increase reservoir volume by increasing chamber length, for example, in reservoirs that may be used in skin-adhered embodiments. In some embodiments, reservoir volumes scale with the cube of their linear dimensions. In some embodiments, a skin adhered system may be less than 12 mm OD. In some embodiments, dimensions and drug solution reservoir volumes for a system of 8 mm thickness are 36×30×8 mm, 1.0 mL; 53×47×8 mm, 2.7 mL; 78×72×8 mm, 7.0 mL. In some embodiments, dimensions and drug solution reservoir volumes for a system of 12 mm thickness may have a volume of 20 mL for a 78×72×12 mm system.

Figure 4A:
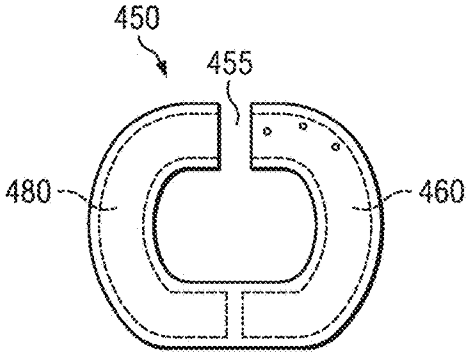
FIG. 4A illustrates a plan view of a reservoir system according to a specific example embodiment of the disclosure.
Figure 4B:
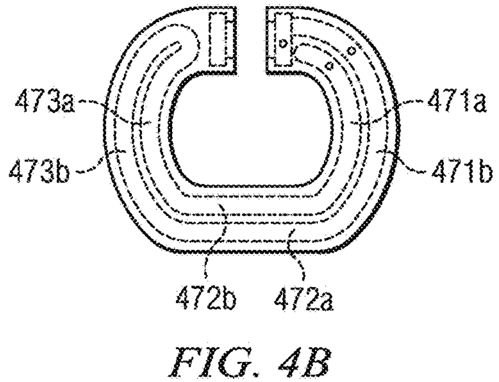
FIG. 4B illustrates a plan view of a 0.9 mL volume reservoir system according to a specific example embodiment of the disclosure.

FIG. 4A illustrates reservoir assembly 450 gap 455, pump fluid chamber 460 and delivery fluid chamber 480. An assembled pump (e.g., as shown in FIG. 3B) may be inserted into gap 455. FIG. 4B illustrates a plan view of a reservoir assembly 450 having a delivery fluid volume of 0.9 mL. A reservoir assembly 450 comprises pump fluid chamber 460 and delivery fluid chamber 480. Pump fluid chamber comprises curvature 471*a* fluidly connected to straight section 472*a*, fluidly connected to curvature 473*a*, fluidly connected by hairpin a 474*a* to curvature 473*b*, fluidly connected to straight section 472*b*, fluidly connected to curvature 471*b*.

Figure 4C:
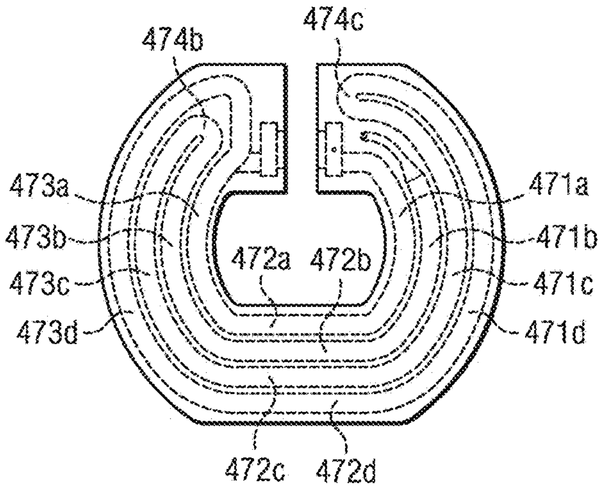
FIG. 4C illustrates a plan view of a 2.7 mL reservoir system according to a specific example embodiment of the disclosure.

FIG. 4C illustrates a reservoir assembly having a delivery volume of 2.7 mL. The pump fluid chamber comprises curvature 471*a*, fluidly connected to straight section 472*a*, fluidly connected to a curvature 473*a*, fluidly connected to straight section 472*a*, fluidly connected to a curvature 473*d*, fluidly connected to a straight section 472*d*, fluidly connected to a curvature 471*d*, fluidly connected to hairpin 474*c*, fluidly connected to a curvature 471*c*, fluidly connected to straight section 472*c*, fluidly connected to hairpin 474*b*, fluidly connected to curvature 473*b*, fluidly connected to straight section 472*b*, fluidly connected to curvature 471*b*, fluidly connected to an air vent.

Figure 4D:
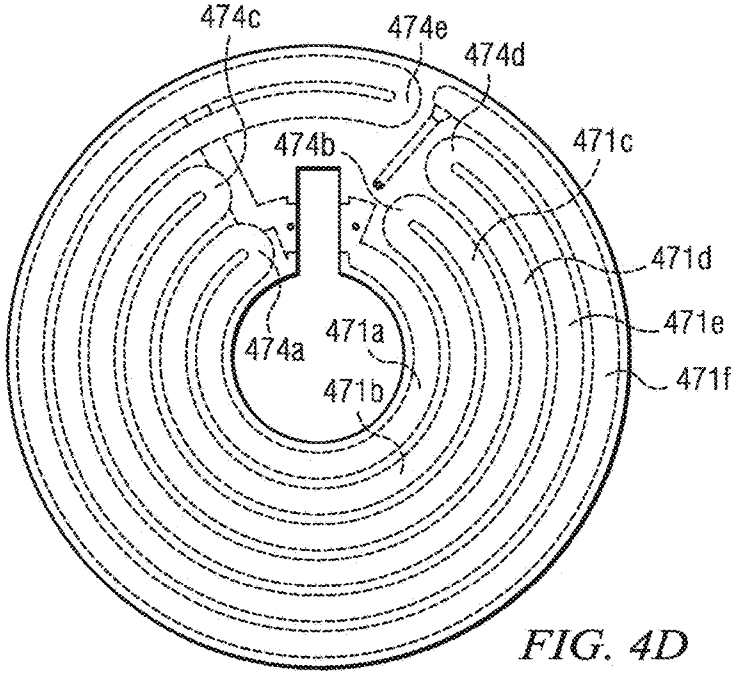
FIG. 4D illustrates a plan view of a 7.3 mL reservoir system according to a specific example embodiment of the disclosure.

FIG. 4D illustrates a reservoir assembly having a delivery volume of 7.3 mL. Pump fluid chamber 460 comprises curvature 471*a*, fluidly connected to hairpin 474*a*, fluidly connected to curvature 471*b*, fluidly connected to hairpin 474*b*, fluidly connected to a curvature 471*c*, fluidly connected to hairpin 474*c*, fluidly connected to curvature 471*d*, fluidly connected to hairpin 474*d*, fluidly connected to curvature 471*e*, fluidly connected to hairpin 474*e*, fluidly connected to curvature 471*f*, fluidly connected to an air vent.

Figure 5A:
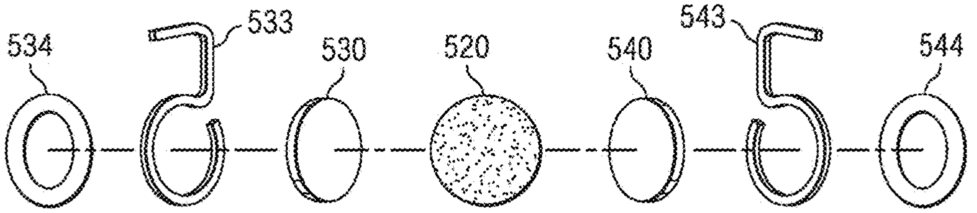
FIG. 5A illustrates an exploded view of a pump according to a specific example embodiment of the disclosure.

In some embodiments, components of a pump system may be manufactured at a low cost. FIG. 5A illustrates an exploded view of a pump according to a specific example embodiment of the disclosure. From left to right, the components are: PVC O-ring 534, gold strip 533, $Ag/Ag_2O$-coated carbon paper anode 530, ceramic membrane 520, $Ag/Ag_2O$-coated carbon paper cathode 540, gold strip 543 and PVC O-ring 544.

In some embodiments, assembled components of a pump system may be inserted into a reservoir gap. In some embodiments, a reservoir may contain a chamber for pumped water and a chamber for a delivery fluid. As displayed in FIGS. 4A-D, delivery fluid reservoir volumes may vary for use with a pump and a system described herein. In some embodiments, a system may comprise a reservoir with one or more hairpins.

Figure 5B:
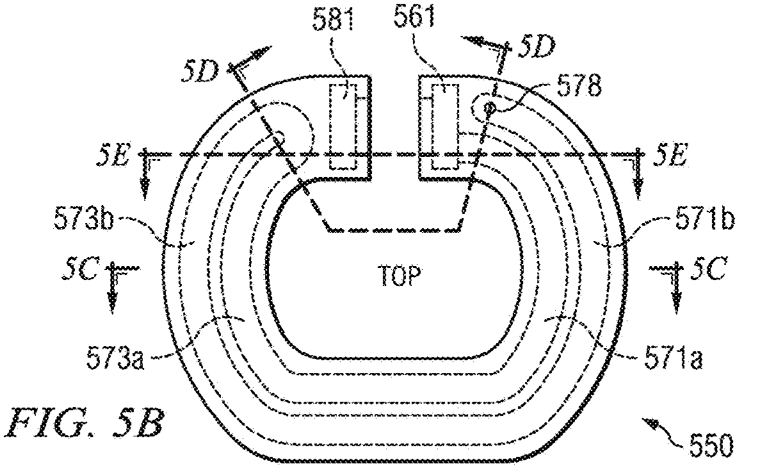
FIG. 5B illustrates a plan view of a reservoir system according to a specific example embodiment of the disclosure.

FIG. 5B illustrates a plan view of the reservoir system according to a specific example embodiment of the disclosure. FIG. 5B depicts a reservoir 550 for pumped water and drug chambers and a pump gap.

In some embodiments, a pump system (e.g., a functional drug infusion system) may comprise a reservoir with two chambers. In some embodiments, a reservoir may comprise a pump fluid chamber and a delivery fluid chamber. In some embodiments, each chamber may comprise an opening, a curved section, fluidly linked to a straight section, fluidly connected to a curved section, fluidly connected to a hairpin, fluidly connected to a curved section fluidly connected to a straight section and fluidly connected to a curved section. In some embodiments, a pump fluid chamber may comprise of a proximal end, medial end, and distal end. In some embodiments, a pump fluid chamber may comprise of a pump coupling. In some embodiments, a reservoir may comprise a pump fluid chamber assembly comprising an air inlet. In some embodiments, a reservoir may comprise a pump fluid chamber assembly comprising a pump fluid chamber fill inlet and septum. In some embodiments, a reservoir may comprise a pump fluid chamber assembly comprising pump fluid chamber distal fill inlet. In some embodiments, a pump fluid chamber may comprise of a proximal end, medial end, and distal end. In some embodiments, a pump fluid chamber may comprise a pump coupling. In some embodiments, a reservoir may comprise a delivery fluid chamber assembly comprising an air inlet. In some embodiments, a reservoir may comprise a delivery fluid chamber assembly comprising a delivery fluid chamber fill inlet and septum. In some embodiments, a reservoir may comprise a delivery fluid chamber assembly comprising a pump fluid fill inlet and septum. In some embodiments, a reservoir may comprise a delivery fluid chamber assembly comprising a delivery fluid outlet. In some embodiments, a delivery fluid chamber may comprise a proximal end, medial end, and distal end. In some embodiments, a delivery fluid chamber may comprise a pump coupling. A reservoir assembly may comprise, in some embodiments, a housing. A housing (e.g., a rigid and/or semi-rigid housing) may, for example, comprise any suitable plastics, polymers, acrylics, and/or other materials. A housing may be transparent and/or or opaque in some embodiments.

In some embodiments, a delivery fluid chamber may be configured to be replaceable and/or disposable. For example, a delivery fluid chamber may be configured as a cartridge that connects to a pump and/or a reservoir, a connection that may be direct or through a connector. A connector may be fixed to a pump, a reservoir, a delivery fluid chamber, or combinations thereof.

Figure 5C:
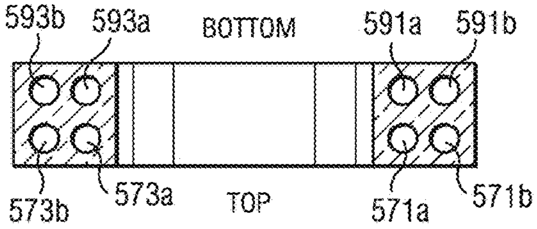
FIG. 5C is a sectional view of a reservoir system according to a specific example embodiment of the disclosure along section lines 5C-5C shown in FIG. 5B.

FIG. 5C is a sectional view of a reservoir system according to a specific example embodiment of the disclosure along section lines 5C-5C shown in FIG. 5B. FIG. 5C illustrates a sectional view of the top and bottom layer inlets and outlets of the reservoir system according to a specific example embodiment of the disclosure. The left side of FIG. 5C depicts the tubular hosing of curvatures 573*a*, 573*b*, 593*a*, 593*b*. Curvatures 573*a* and 573*b* are stacked directly over curvatures 593*a* and 593*b*. The right side of FIG. 5C depicts the tubular hosing of curvature 571*a*, 571*b*, 591*a*, 591*b*. Curvatures 571*a* and 571*b* are stacked directly over curvatures 591*a* and 591*b*.

Figure 5D:
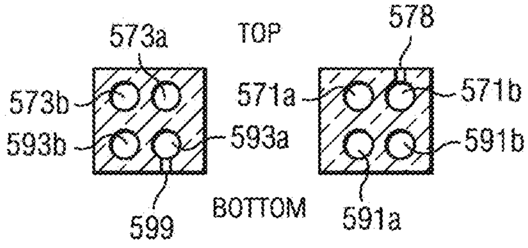
FIG. 5D is a sectional view of a reservoir system according to a specific example embodiment of the disclosure along section lines 5D-5D shown in FIG. 5B.

FIG. 5D is a sectional view of a reservoir system according to a specific example embodiment of the disclosure along section lines 5D-5D shown in FIG. 5B. The left side of FIG. 5D depicts the left side of reservoir 550, including delivery fluid outlet 599 of delivery fluid chamber 580. The left side of FIG. 5D depicts the tubular hosing of curvature 573*a*, 573*b*, 593*a*, 593*b*. Curvatures 573*a* and 573*b* are stacked directly over curvatures 593*a* and 593*b*, respectively. Curvature 593*a* also connects to delivery fluid outlet 599. The right side of FIG. 5D depicts the right side of reservoir 550, including air inlet 578 of the water chamber 560. The right side of FIG. 5D depicts the tubular hosing of curvatures 571*a*, 571*b*, 591*a*, 591*b*. Curvatures 571*a* and 571*b* are stacked directly over curvatures 591*a* and 591*b*.

Figure 5E:
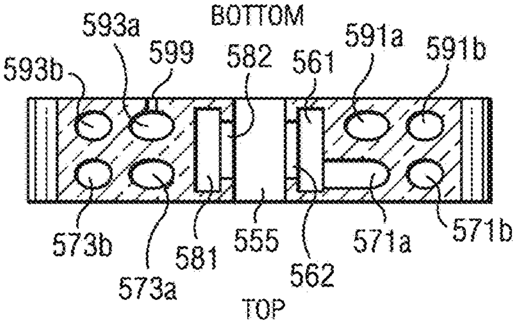
FIG. 5E is a sectional view of a reservoir system according to a specific example embodiment of the disclosure along section lines 5E-5E shown in FIG. 5B.

FIG. 5E is a sectional view of a reservoir system according to a specific example embodiment of the disclosure along section lines 5E-5E shown in FIG. 5B. This view illustrates gap 555, into which a pump may be inserted, and couplings 561 and 581 to which a pump may be fluidly coupled. It also illustrates delivery fluid outlet 599.

FIG. 5F illustrates an elevation view of the reservoir system shown in FIG. 5B according to a specific example embodiment of the disclosure. FIG. 5F depicts the delivery fluid outlet.

FIG. 5G is a sectional view of a reservoir system according to a specific example embodiment of the disclosure along section lines 5G-5G shown in FIG. 5F. FIG. 5G depicts a water chamber of the reservoir system according to a specific example embodiment of the disclosure. An opening of the water chamber is fluidly connected to first curvature 571*a*, fluidly connected to straight section 572*a*, fluidly connected to second curvature 573*a*, fluidly connected to hairpin 574, fluidly connected to first curvature 573*b*, fluidly connected to straight section 572*b*, fluidly connected to second curvature 571*b*. FIG. 5G also depicts water chamber air inlet 578.

FIG. 5H illustrates a sectional view of a reservoir system according to a specific example embodiment of the disclosure along section lines 5H-5H shown in FIG. 5F. FIG. 5H depicts delivery fluid chamber 580 of a reservoir system, in which the opening of delivery fluid chamber 580 is fluidly connected to first curvature 593*b*, fluidly connected to straight section 592*b*, fluidly connected to a second curvature, fluidly connected to hairpin 594, fluidly connected to first curvature 591*a*, fluidly connected to straight section 592*a*, fluidly connected to second curvature 593*a*.

In some embodiments, a top chamber may comprise pumped water. In some embodiments, a bottom chamber may comprise a delivery fluid solution. In some embodiments, a diameter channel for a chamber may be less than 3 mm. In some embodiments, a channel diameter (e.g., ID and/or OD) may vary along its length.

FIG. 5I illustrates a generally isometric view of the reservoir system shown in FIGS. 5B-5H. FIG. 5I depicts the water chamber proximal fill inlet 563. FIG. 5I depicts the opening on the left top layer of the water chamber which comprises a cone or funnel 562.

Figure 5J:
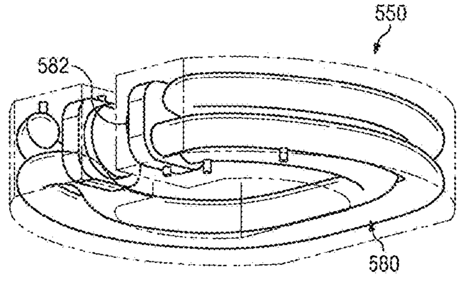
FIG. 5J illustrates a generally isometric view of the reservoir system shown in FIGS. 5B-5I.

FIG. 5J illustrates a generally isometric view of the reservoir system shown in FIGS. 5B-5I. FIG. 5J depicts the opening on the right bottom layer of the delivery fluid chamber, which comprises a cone or funnel 582.

Pump Systems

Pumps may be configured to deliver medications continuously and/or intermittently according to some embodiments. For example, insulin pumps used by patients with diabetes, particularly Type 1 diabetes, may be programmed to deliver insulin continuously at a basal delivery rate, in accordance with a programmed or programmable delivery profile(s), and also may be programmed to deliver insulin boluses (e.g., specific doses of a drug delivered in a predetermined time period, for example, less than 1 hour, less than 30 minutes, less than 10 min, and/or less than 5 min.), usually in conjunction or anticipation of carbohydrate intake (e.g., meals) or anticipated or onset of glycemic excursions. While insulin increases the consumption of glucose by cells of the body, glucagon induces conversion of stored glycogen to glucose, increasing the concentration of glucose in body fluids. In the management of diabetes, a pump system may deliver glucagon and/or insulin. A two-pump system comprising both an insulin pump and a glucagon pump may be of particular value in diabetes management because it may allow both up and down adjustment of the glycemia and may decrease the duration and/or likelihood of the unwanted hyperglycemic and/or hypoglycemic periods.

Pumps may be configured to deliver drugs (e.g., continuously and/or intermittently) that are useful in managing Parkinson's disease, for example, drugs typically having in-vivo half-lives of less than 4 hours (e.g., between about 30 min and about 3 hours, between 1 hour and 2 hours). Examples of drugs that may be useful in managing Parkinson's disease include water soluble L-DOPA prodrugs, apomorphine, lisuride, L-DOPA decarboxylase inhibitors and/or catechol-O-methyl transferase inhibitors.

Fluid pumps (e.g., drug pumps) may also be used to deliver a solution of a drug (e.g., a biological and/or chemical) having a short half-life in the body of a subject. Examples of short-lived chemicals may include, in some embodiments, short-lived antibiotics, like gentamicin, tobramycin and cefotaxime. Gentamicin is not well absorbed when orally administered, but is well absorbed when subcutaneously and intramuscularly delivered. Its elimination half-life in patients with normal renal function may be as short as 2 hours, making its continuous and/or frequent delivery potentially advantageous. Gentamicin may be used, for example, in the treatment of severe infections by Gram-negative bacteria like *Streptococcus aureus* and is used, for example, in treating septicemia, neonatal sepsis, neonatal meningitis, biliary tract infection, pyelonephritis, prostatitis and endocarditis. Tobramycin may have a serum half-life in normal individuals of about 2 hours. It may be effective, for example, against pneumonia, particularly when caused by *Pseudomonas aeruginosa*. Cefotaxime has an elimination half-life of merely 1.1 hours, making its continuous and/or frequent pumping potentially of particular interest. It may be effective in treatment of infections of the respiratory tract, skin, bones, joints, urogenital system, meningitis, and septicemia caused by many Gram-negative bacteria. It is, for example, active against penicillin-resistant strains of *Streptococcus pneumoniae.*

In some embodiments, active pharmaceutical ingredients that may be pumped include, heparin (e.g., used to control blood coagulation), interferon (e.g., used in the therapy of C-type hepatitis) or ketamine (e.g., used in pain management, for example, in conjunction with opioid drugs like morphine and its derivatives). Pumping in accordance with some embodiments of the disclosure may also be desirable (e.g., advantageous) when therapy is better achieved by maintaining a substantially constant concentration of a drug or substance in a body fluid, such as serum, and/or when therapy requires selective drug delivery to targeted organ or tissue (e.g., as is the case in chemotherapy of most cancers).

Systems comprising the pumps can also be configured to deliver multiple drugs from multiple reservoirs, for example two drugs from two separate reservoirs. Delivery from separate reservoirs can be simultaneous or non-simultaneous (e.g., staggered, sequential, overlapping, intermittent). For example a first fluid (e.g., comprising a drug) may be delivered from a first reservoir for a first period at a first flow rate followed by delivery of a second fluid (e.g., comprising a drug) from a second reservoir for a second period at a second flow rate.

In some embodiments, a device delivering fluids (e.g., drugs) may include a pump (e.g., drug pump, insulin pump), a reservoir, a controller, one or more sensors, or combinations thereof. A fluid pump system (e.g., a medication pump system) may comprise, in some embodiments, flow-causing components, metering components (e.g., accurate drug dosing components), and/or an implanted needle or cannula, the needle or cannula connected through a plastic tubing to a flow-causing pump. A fluid delivery system may pump- and/or deliver a defined volume of a fluid (e.g., drug containing solution and/or a solution containing multiple drugs), stored in a reservoir. A needle may be optionally short, its length between about 0.3 cm and about 1 cm, and its gauge may be, for example, between about 22 and about 32 and/or between about 26 and about 29. A needle (e.g., a narrow gauge needle), may be optionally inserted in order to reduce the extent to which its presence is felt by the wearer of the skin-attached drug pumping system in the skin of the belly, the tip of the needle residing in the fatty tissue may often be found below the skin of the belly. A needle may be inserted in an intravenous port in some embodiments. A delivery fluid, according to some embodiments, may comprise a pharmaceutical agent used to treat a condition requiring treatment in humans or in animals, a nutrient, a nutrient supplement, and/or a vaccine. Insulin may be an example of a drug in some embodiments. A delivery fluid comprising a drug may further include a solution in which the drug may be dissolved and/or dispersed.

A pump system, in some embodiments, may comprise a reference electrode. For example, a reference electrode may be included to monitor potentials relative to an anode and/or a cathode. A reference electrode may be desired, in some embodiments, to monitor the presence of reactant. For example, the potential between an anode and a reference electrode or between a cathode and a reference electrode may rise when reactant at the anode or cathode, respectively, has been depleted. A controller may be configured to terminate flow upon detecting a potential relative to a reference electrode within a range (e.g., a predetermined range) and/or above a threshold (e.g., a preset threshold).

In some embodiments, a volume and/or delivery rate of a drug or drug solution, described herein, may be controlled by a pump system. In some embodiments, a pump system may comprise a pump connected to a computer (e.g., a personal computer, microcontroller, or the like) via an external interface. In some embodiments, a system may be controlled, for example by an external interface comprising an interface cable for an external interface option to an external controller comprising a 3V lithium battery, and one or more control buttons. In some embodiments, control buttons may allow, for example, programming of a current to be applied to a pump, and time duration of such application. In some embodiments, a system may comprise a transmitter and/or receiver. In some embodiments, a system may comprise an alarm. In some embodiments, a system may comprise a reusable, removable ("pop-out") electronic package in its center. In some embodiments, an electronic package may comprise a constant current supply and an LCD or an electrophoretic (e.g., E-sink) or another display. In some embodiments, a removable electronic package may comprise an electrically coupled processor, memory, user interface, (i.e., one or more control buttons) and a power source. In some embodiments, an electronic system may comprise a wireless controller. In some embodiments, an electronic system may comprise RF communication. In some embodiments, an electronic system may comprise blue-tooth technology. A controller may be contained within the unit that is physically connected to a pump (e.g., a catheter) or it may be spaced away and/or operate remotely in some embodiments. A controller may be contained, for example in a wrist watch and/or a mobile communication device (e.g., a cell phone).

Figure 6B:
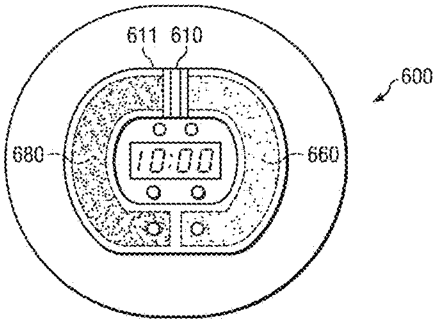
FIG. 6B illustrates a plan view of a pump system according to a specific example embodiment of the disclosure.
Figure 6A:
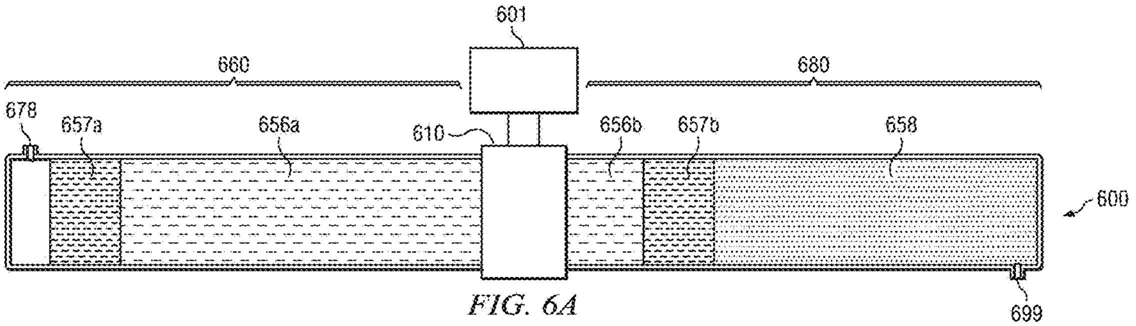
FIG. 6A illustrates an elevation view of a pump system according to a specific example embodiment of the disclosure.

FIG. 6A illustrates an elevation view of pump system 600 comprising pump 610, pump fluid chamber 660, delivery fluid chamber 680, air-inlet 678, delivery fluid outlet 699, and controller 601, according to a specific example embodiment of the disclosure. Compared to FIG. 6B, pump fluid chamber 660 and delivery fluid chamber have been straightened, for illustration purposes, to be collinear with pump 610. FIG. 6A depicts a pump fluid chamber 660 filled with a separator 657*a* in fluid communication with a first aliquot of pump fluid 656*a* and delivery fluid chamber 680 is filled with a second aliquot of pump fluid 656*b*, in fluid communication with separator 657*b* and fluidly connected to delivery fluid 658. A separator may be a liquid or a solid. Examples of a liquid separator may include, for example, silicone oil or a glycerol mono or di-ester of a fatty acid. Solid separators may be plastic, ceramic or metallic in some embodiments. Once pumping begins pump fluid 656*a* from pump fluid chamber 660 passes through pump 610 and begins to accumulate in delivery fluid chamber 680 and push separator 657*b*, which pushes delivery fluid 658 to outlet 699.

Figure 6C:
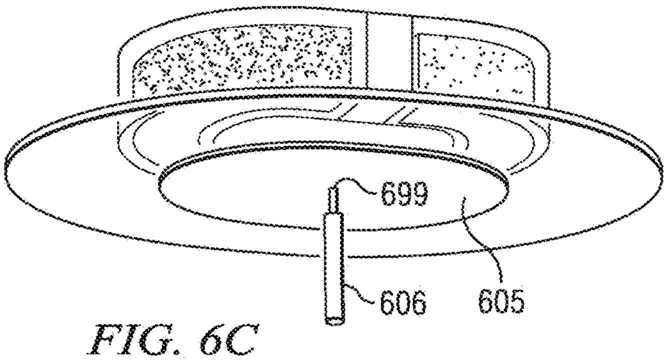
FIG. 6C illustrates an isometric view of a pump system according to a specific example embodiment of the disclosure.
Figure 6D:
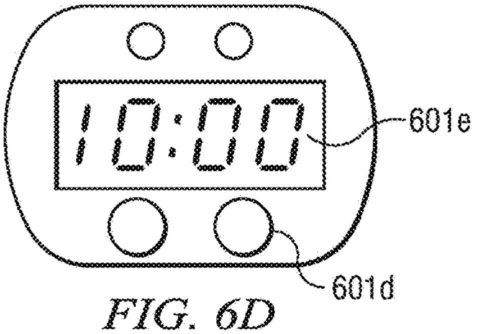
FIG. 6D illustrates a plan view of a constant current/voltage controller and timer according to a specific example embodiment of the disclosure.

FIG. 6B illustrates miniature skin-adhered fluid-delivery system 600 shown in FIG. 6A in accordance with certain exemplary embodiments. FIG. 6B depicts a delivery fluid chamber 680, pump 610, controller 601, and pump fluid chamber 660. Delivery fluid 658 (e.g., a drug-containing solution) is densely speckled and pump fluid 656 is lightly speckled. The structure at the top-center of FIG. 6B (i.e., separating pump fluid compartment 660 from delivery fluid compartment 680) depicts electro-osmotic pump 610 disclosed herein. Its outer diameter is 8 mm. The large transparent plastic disc mimics the skin. It is penetrated by a 5 mm long 29 gauge syringe needle 606 as shown in FIG. 6C. System 600 is adhered to the transparent plate that mimics the skin with two-sided adhesive tape 605. As depicted, system 600 has reusable, removable ("pop-out") electronic package 601 in its center (FIG. 6D-5G). As depicted in the embodiment of FIG. 6B, pump fluid chamber 660 of system 600 may contain pump fluid 656*a* and delivery fluid chamber 680 may contain delivery fluid 658 (e.g., insulin mimic), which does not pass through pump 610. According to this embodiment, a pump's active area may be about 0.3 $cm^2$. Delivery fluid chamber 680 may also include separator 657*b* separating pump fluid 656*b* and delivery fluid 658. During operation, separator 657*b* moves as pump fluid 656*b*, shown colorless, displaces delivery fluid 658.

The large transparent plastic disc to which system 600 is attached, mimics skin for illustration purposes and may be replaced in actual use by human or animal skin. This plastic disc is penetrated by syringe needle 606 as shown in FIG. 6C. FIG. 6C illustrates an isometric view of a pump system according to a specific example embodiment of the disclosure. When delivery fluid 658 is pushed out of the drug outlet 699 it reaches needle 606, which is inserted into a subject. FIG. 6C depicts an embodiment comprising an adhesive patch 605 for attachment of the system to a subject. In some embodiments, the needle may be an about 5 mm long, about 29 gauge syringe needle 606. According to the depicted embodiment, the system is adhered to the transparent plate that mimics the skin with two-sided adhesive tape 605. In other embodiments, a system may be attached to a subject using an elastic band. Optionally, a needle may be longer than about 5 mm (e.g., longer than about 7 mm), and/or shorter than 9 mm. In some embodiments, a needle may be inserted in a subject (e.g., the skin). The angle of insertion (e.g., relative to the plane of the skin) may be from 15° to about 45° versus the plane of the skin. The angle of insertion (e.g., relative to a line normal to the skin) may be from about 75° to about 45°. A needle may have a diameter from about 31 gauge to about 23 gauge.

FIG. 6D illustrates a plan view of a constant current/voltage controller and timer according to a specific example embodiment of the disclosure. FIG. 6D depicts a controller 601, comprising a user interface 601*d*, LCD display 601*e*, an electrically coupled processor, memory, and power source. As depicted controller 601 of FIG. 6D further comprises two control buttons 601*d* for programming of the current to be applied to pump 610, and the time (e.g., duration and/or interval) of such application. These two settings (i.e., the combination of current and time) may define the delivered volume and/or the delivery rate (i.e., the flow rate). According to the depicted embodiment, the dimensions of the system are 36 mm×30 mm×8 mm.

Figure 6E:
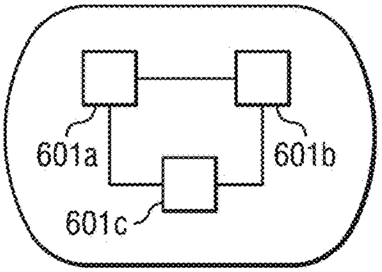
FIG. 6E illustrates a plan view of a constant current/voltage controller and timer according to a specific example embodiment of the disclosure.

FIG. 6E illustrates a plan view of a constant current/voltage controller and timer according to a specific example embodiment of the disclosure. FIG. 6E depicts an electrically coupled processor 601*a*, memory 601*b*, and power source 601*c*.

Figure 6F:
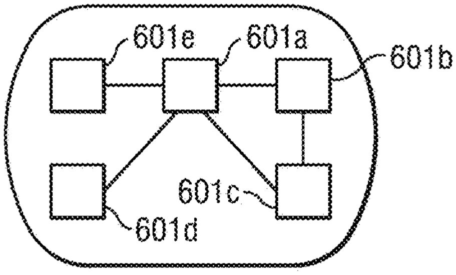
FIG. 6F illustrates a plan view of a constant current/voltage controller and timer according to a specific example embodiment of the disclosure.

FIG. 6F illustrates an exploded view of the controller shown in FIG. 6E according to a specific example embodiment of the disclosure. FIG. 6F depicts a processor 601*a*, memory 601*b*, and power source 601*c* electrically coupled, and a LCD display 601*e* and user interface 601*d*.

Figure 7A:
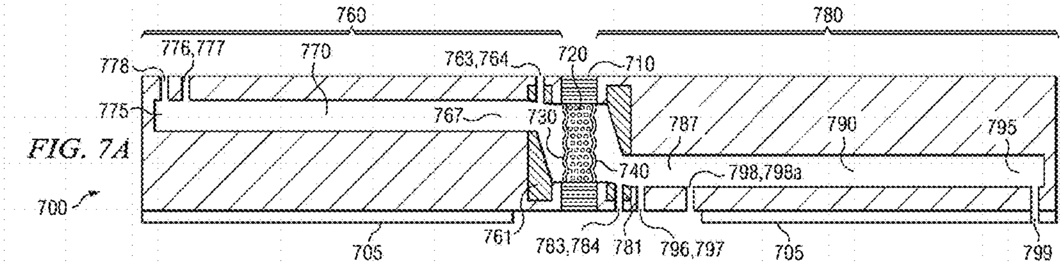
FIG. 7A illustrates a sectional view of a pump system according to a specific example embodiment of the disclosure.
Figure 7B:
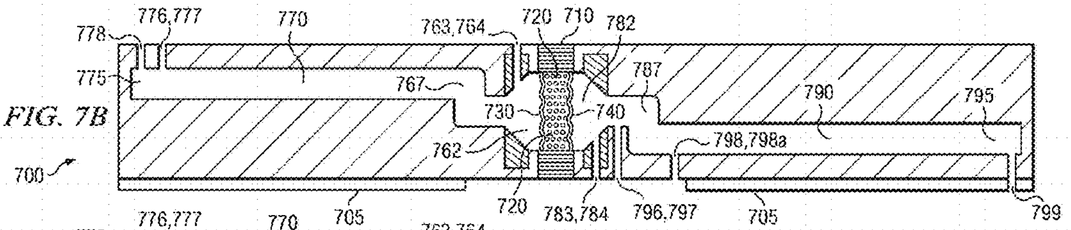
FIG. 7B illustrates a sectional view of a pump system according to a specific example embodiment of the disclosure.
Figure 7C:
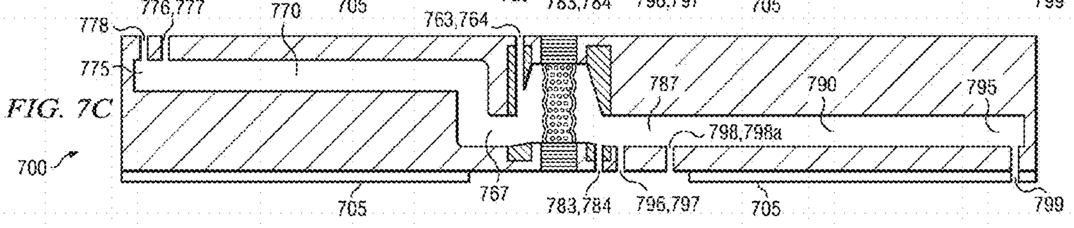
FIG. 7C illustrates a sectional view of a pump system according to a specific example embodiment of the disclosure.

FIGS. 7A-7C illustrate embodiments of system 700 comprising a reservoir assembly in which pump fluid chamber 760 and delivery fluid chamber 780 have been rendered, for illustration purposes, as coplanar with each other and with pump 710 similar to the collinear arrangement shown in FIG. 6A. Pump fluid chamber 760 and delivery fluid chamber 780 may be configured as illustrated or may be configured such that pump fluid chamber 760 substantially overlays delivery fluid chamber 780 and the two together define, at least partially, an oval and/or a circle (e.g., as shown in FIGS. 4B-4D).

FIG. 7A illustrates a sectional view of pump system 750 according to a specific example embodiment of the disclosure. Pump 710 comprises membrane 720, anode 730, and cathode 740. Pump fluid chamber assembly 760 depicted in FIG. 7A, is located to the left of pump 710 and pump fluid chamber opening 765 is coupled with pump coupling 761, which is fluidly coupled to pump 710. Coupling 761 includes a cone, the diameter of which expands (from left to right) from the insider diameter of pump fluid chamber 760 to the diameter of membrane 720. FIG. 7A depicts a proximal end 767, a medial portion 770 and a distal end 775 of pump fluid chamber 760. Pump fluid chamber 760 comprises 3 external fluid connections, namely air inlet 778 for admitting air into pump fluid chamber 760 during pump operation; separator distal fill inlet 776 and septum 777 for installing a volume (e.g., a small volume) of a separator fluid in pump fluid chamber 760; and pump fluid inlet 763 and septum 764 for loading a volume (e.g., a small volume) of pump fluid in pump fluid chamber 760 in contact with pump 710.

Pump 710 is fluidly connected to delivery fluid chamber assembly 780 via pump coupling 781 through a delivery fluid chamber opening 785 of the delivery fluid chamber 780. Coupling 781 includes cone 782, the diameter of which narrows (from left to right) from the diameter of membrane 720 to the insider diameter of delivery fluid chamber 780. Delivery fluid chamber 780 comprises a proximal end 787, medial portion 790 and distal end 795. Medial portions 770 and 790 may include various curvatures, straight sections, and/or hairpins according to some embodiments (e.g., FIGS. 4B-4D). Proximal end 767 and 787 and distal ends 775 and 795 may independently include various curvatures, straight sections, and/or hairpins according to some embodiments. Delivery fluid chamber 780 also comprises 4 external fluid connections, namely pump fluid inlet 783 and septum 784 for loading a volume (e.g., a small volume) of pump fluid in delivery fluid chamber 780 in contact with pump 710; separator fluid inlet 796 and septum 797 for installing a volume (e.g., a small volume) of a separator fluid in delivery fluid chamber 780; delivery fluid inlet 798 and septum 798*a* for installing a volume of a delivery fluid in delivery fluid chamber 780 (e.g., filling chamber 780); and delivery fluid outlet 799.

FIG. 7B illustrates a sectional view of pump system 750 according to a specific example embodiment of the disclosure. FIG. 7B depicts the same components depicted in FIG. 7A. FIG. 7C illustrates a sectional view of pump system 750 according to a specific example embodiment of the disclosure. FIG. 7C depicts the same components depicted in FIG. 7A. In some embodiments, the shape and/or relative location of coupling 761, cone 762, opening 765, coupling 781, cone 782, and/or opening 785 may impact the flow of fluids through pump 710. It may be desired and/or required to arrange coupling 761, cone 762, opening 765, coupling 781, cone 782, and/or opening 785 in an oblique configuration (e.g., FIG. 7A), a linear, centered configuration (e.g., FIG. 7B), a linear, off-center configuration (e.g., FIG. 7C).

In some embodiments, an outer diameter of an electroosmotic pump may be about 1 cm or less, for example, about 0.8 cm or less. Thus the cross-sectional area of a pump may be less than 1 $cm^2$, less than 0.8 $cm^2$, and/or about 0.5 $cm^2$ or less. In some embodiments, a pump may be powered by a small cylindrical, optionally coin-type, battery with an OD of, for example, less than 13 mm, less than 8 mm, and/or less than 6 mm. A battery may be a nominally about 1.4 V open circuit voltage (OCV) alkaline Zn-air battery. Alternatively, a pump may be powered by a nominally about 1.4 V OCV alkaline Zn-manganese dioxide battery, or by a nominally about 1.6 V OCV Zn-silver oxide battery, or by a nominally about 2.8 V or higher OCV lithium anode battery, such as the 3.2 V OCV Li-manganese dioxide battery. A pump in some embodiments may provide a flow rates of about 1-40 μL/min. In some embodiments, with an about 3 V OCV lithium anode battery, a flow rate of between about at least 20 μL/min and about 40 μL/min may be sustained. In some embodiments, a flow rate between about 3 μL/min and about 20 μL/min may be sustained with a 1.4 V zinc-manganese dioxide alkaline battery. Some examples of small batteries that can be used are shown in Table 1. All have sufficient capacity for electro-osmotically pumping at least about 16 mL of the solutions disclosed here, containing enough insulin for at least about a month or about 100 meals.

According to some embodiments, a pump system may comprise one or more sensors. For example, a pump may contain a sensor for detection of the volume of delivery fluid administered to a subject. Delivery fluid volume may be assessed by, for example, monitoring the position of a separator. In some embodiments, a separator may be colored (e.g., using a visible ink or dye, a luminescent agent, a phosphorescent agent, or the like). A sensor (e.g., a photosensitive film) may be positioned sufficiently close to the marked separator to permit the film to detect separator movement (e.g., adhered to a pump system housing). A sensor may be arranged in communication with a controller, according to some embodiments. A controller in communication with a sensor may adjust the potential difference and/or a current across a membrane (e.g., to adjust delivery to a desired flow rate, dose, volume, duration, or the like).

TABLE 1

Exemplary Useful Batteries

| Battery | Stock number | Thickness | OD | Weight | Voltage | Capacity |
|---|---|---|---|---|---|---|
| Zinc Air | L10ZA | 3.6 mm | 5.8 mm | 0.31 g | 1.4 V | 84 mW · h |
| Silver Oxide | Energ.364/363 | 2.15 mm | 6.80 mm | 0.37 g | 1.55 V | 28 mW · h |
| Silver Oxide | Energ.377/376 | 2.60 mm | 6.80 mm | 0.42 g | 1.55 V | 32 mW · h |
| Lithium | Energ.CR1025 | 2.50 mm | 10.00 mm | 0.70 g | 3.0 V | 60 mW · h |
| Lithium | Energ.CR1220 | 2.00 mm | 12.50 mm | 0.78 g | 3.0 V | 80 mW · h |

Loading Methods for Pump Systems

FIGS. 8A-8E illustrate steps for loading reservoir assembly 850 (shown only FIGS. 8D-8E) in which pump fluid chamber 860 and delivery fluid chamber 880 have been rendered, for illustration purposes, as coplanar with each other and with pump 810 similar to the collinear arrangement shown in FIG. 6A and FIGS. 7A-7C. Pump fluid chamber 860 and delivery fluid chamber 880 may be configured as illustrated or may be configured such that pump fluid chamber 860 substantially overlays delivery fluid chamber 880 and the two together define, at least partially, an oval and/or a circle (e.g., as shown in FIGS. 4B-4D).

Figures 8A, 8B, 8C:
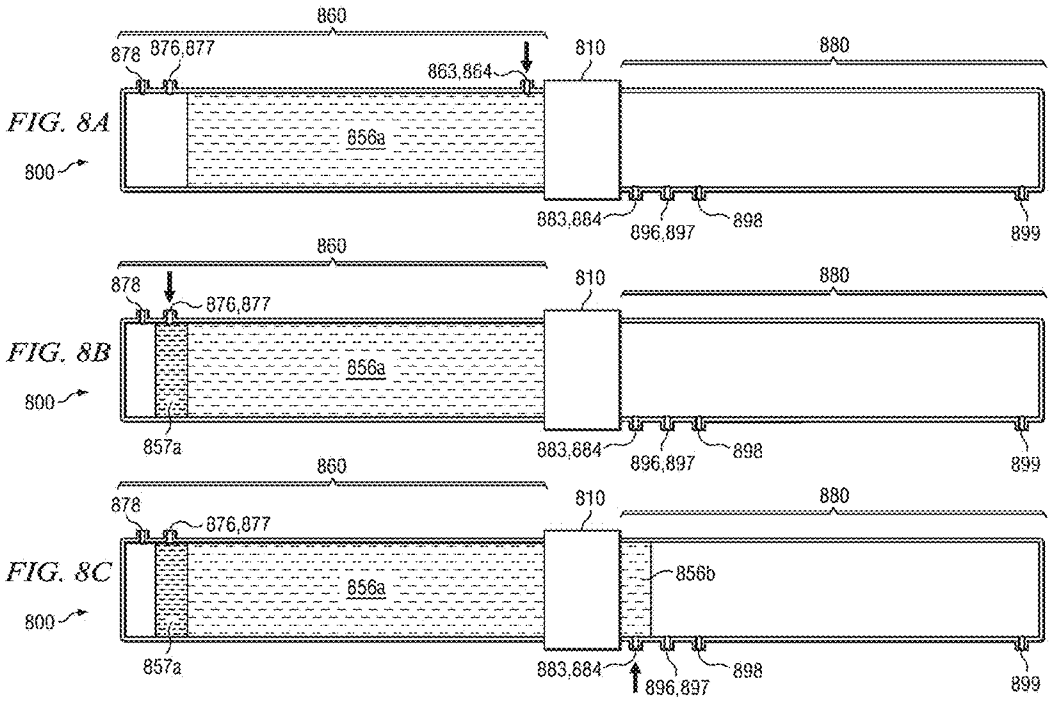
FIG. 8A illustrates a sectional view of a pump system according to a specific example embodiment of the disclosure in which the water chamber is being filled with water.
FIG. 8B illustrates a sectional view of the pump system shown in FIG. 8A in which the water-filled water chamber is being capped with oil according to a specific example embodiment of the disclosure.
FIG. 8C illustrates a sectional view of the pump system shown in FIG. 8B in which the drug chamber is being filled with a water primer according to a specific example embodiment of the disclosure.
Figure 8D:
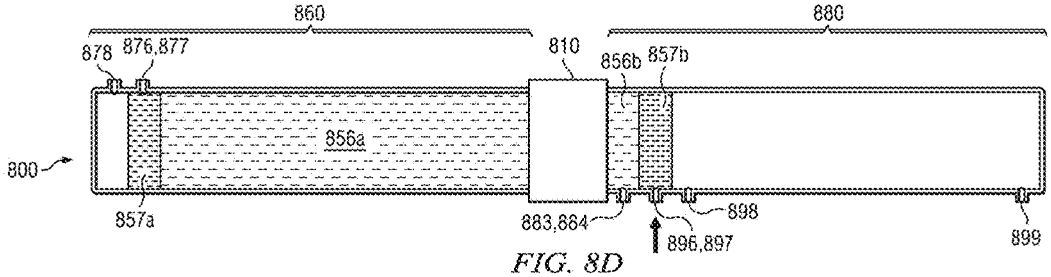
FIG. 8D illustrates a sectional view of the pump system shown in FIG. 8C in which the drug chamber is being filled with an oil separator according to a specific example embodiment of the disclosure.
Figure 8E:
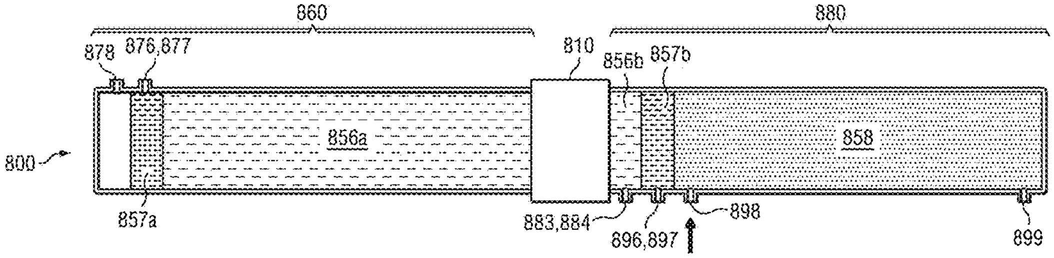
FIG. 8E illustrates a sectional view of the pump system shown in FIG. 8D in which the drug chamber is being filled with a drug-containing fluid according to a specific example embodiment of the disclosure.

FIG. 8A illustrates a sectional view of pump system 800 in which pump fluid chamber 860 is loaded with pump fluid 856a through pump fluid inlet (arrow) according to a specific example embodiment of the disclosure. FIG. 8B illustrates a sectional view of pump system 800 in which pump fluid chamber 860 is loaded with separator fluid 857a through separator fluid inlet 876 (arrow) according to a specific example embodiment of the disclosure. FIG. 8C illustrates a sectional view of pump system 800 in which delivery fluid chamber 880 is loaded with pump fluid 856b through pump fluid inlet 883 (arrow) according to a specific example embodiment of the disclosure. FIG. 8D illustrates a sectional view of pump system 800 in which delivery fluid chamber 880 is loaded with separator fluid 857b through separator fluid inlet 896 (arrow) according to a specific example embodiment of the disclosure. FIG. 8E illustrates a sectional view of pump system 800 in which delivery fluid chamber 880 is loaded with delivery fluid 858 through delivery fluid inlet 898 (arrow) according to a specific example embodiment of the disclosure.

Figure 9A:
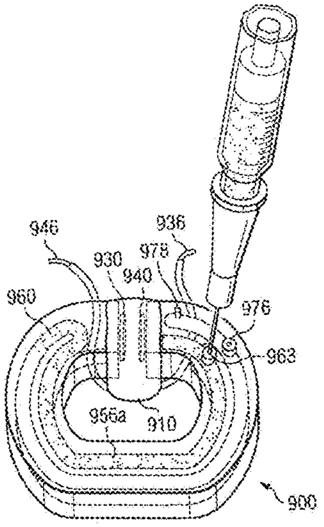
FIG. 9A illustrates an isometric view of a pump system according to a specific example embodiment of the disclosure in which the water chamber is being filled with water.
Figure 9B:
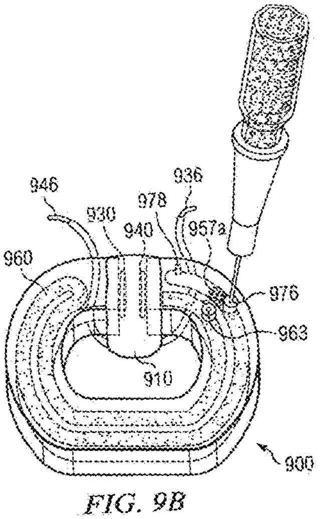
FIG. 9B illustrates an isometric view of the pump system shown in FIG. 9A in which the water-filled water chamber is being capped with oil according to a specific example embodiment of the disclosure.
Figure 9C:
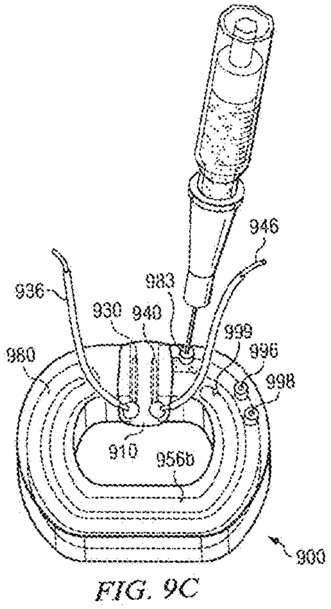
FIG. 9C illustrates an isometric view of the pump system shown in FIG. 9B (flipped over relative to FIG. 9B) in which the drug chamber is being filled with a water primer according to a specific example embodiment of the disclosure.
Figure 9D:
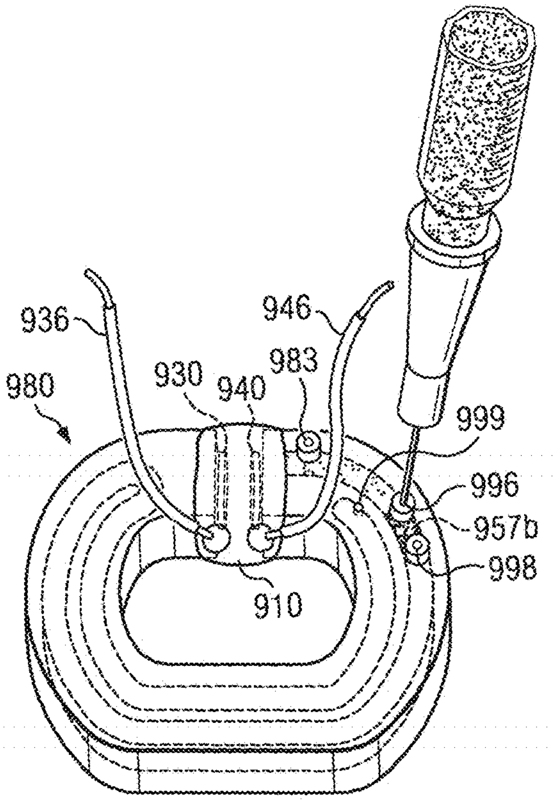
FIG. 9D illustrates an isometric view of the pump system shown in FIG. 9C in which the drug chamber is being filled with an oil divider according to a specific example embodiment of the disclosure.
Figure 9E:
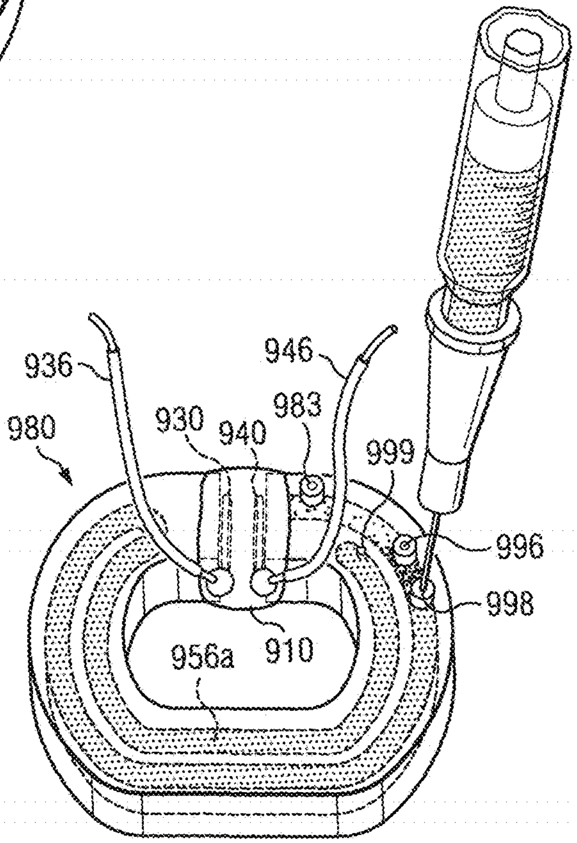
FIG. 9E illustrates an isometric view of the pump system shown in FIG. 9D in which the drug chamber is being filled with a drug-containing fluid according to a specific example embodiment of the disclosure.

FIGS. 9A-9E illustrate steps for loading pump system 900, which comprises pump 910, water chamber 960, and drug solution chamber 980 and parallel FIGS. 8A-8E. Wires 936 and 946 are in electrical communication with anode 930 and cathode 940, respectively, of pump 910. FIG. 9A illustrates an isometric view of pump system 900 in which water chamber 960 is loaded with water 956a through water inlet 963 according to a specific example embodiment of the disclosure. FIG. 9B illustrates an isometric view of pump system 900 in which water chamber 960 is loaded with oil 957a (black) through oil inlet 976 according to a specific example embodiment of the disclosure. FIG. 9C illustrates an isometric view of pump system 900 (flipped over relative to FIG. 9B) in which drug solution chamber 980 is loaded with drug solution 956b through drug solution inlet 983 according to a specific example embodiment of the disclosure. FIG. 9D illustrates an isometric view of pump system 900 in which drug solution chamber 980 is loaded with oil 957b (black) through oil inlet 996 according to a specific example embodiment of the disclosure. FIG. 9E illustrates an isometric view of pump system 900 in which drug solution chamber 980 is loaded with a drug solution 958 (speckled) through drug solution inlet 998 according to a specific example embodiment of the disclosure. In some embodiments, drug outlet 999 may be fluidly connected to a catheter or needle inserted into a subject (e.g., when used). It may be desirable and/or required, according to some embodiments, to complete one or more of the loading steps shown in FIGS. 9A, 9B, 9C, 9D, and/or 9E in a one or more facilities (e.g., manufacturing facilities). In some embodiments, an end user may optionally complete one or more of the loading steps shown in FIGS. 9A, 9B, 9C, 9D, and/or 9E. For example, an end user may complete the loading step shown in FIG. 9E (e.g., immediately prior to use).

In addition, a reservoir may be configured and arranged to be prefilled with a fluid and/or interchangeably engaged with a pump. A prefilled reservoir may be loaded, in some embodiments, as otherwise disclosed herein. According to some embodiments, a prefilled reservoir may be loaded through a fluid chamber opening proximal to where it engages a pump (e.g., a reservoir gap). A removable plug may be positioned over a fluid chamber opening to reduce or prevent fluid loss after loading and prior to pump engagement. For example, a single, removable plug having opposing covers may be positioned in a reservoir gap such that the respective chamber openings are occluded by the covers. In some embodiments, a plug may be positioned to cover opposing reservoir chambers and still allow a pump to be engaged with a reservoir gap. For example, a reservoir gap may receive a pump from one face and permit removal of a plug (e.g., a strip of tape) from the opposite face once the pump is engaged. A plug, pump, and/or reservoir may be configured such that engaging the pump concurrently displaces the plug in some embodiments. Plug removal and/or pump engagement may be performed without introducing fluid leaks (e.g., gas into a reservoir or liquid release from a reservoir).

In some embodiments, a disposable cartridge (reservoir) may have one or more septums (e.g., elastomeric septums). Fluid communication with the contents of a disposable cartridge (e.g., a chamber) may be established by piercing a septum, for example, with a hollow needle (e.g., a steel needle). A prefilled reservoir may comprise, in some embodiments, two chambers, each about completely filled, one with a pump fluid and the other with a delivery fluid, and each having an end at least partially defined by a septum (e.g., a rubber septum).

Pump System Operation

According to some embodiments, a fluid pump system (e.g., a medication pump system) may deliver a fluid (e.g., an insulin solution and/or suspension) stored in a reservoir connected by a tubing to a cannula implanted or a hollow needle in a body tissue. A fluid may be delivered, for example, subcutaneously, optionally into fatty tissue. According to some embodiments, a cannula, (e.g., a plastic cannula) and/or a high gauge (e.g., fine) hollow needle (e.g., a stainless steel needle), for example a 27, 28, 29, 30 or 31 gauge needle, may be implanted in the body of a subject for fluid delivery. A cannula and/or needle may be connected through a plastic tubing to the source of a pumped fluid (e.g., drug). For the intravenous delivery a hollow needle (e.g., connected to a fluid pump through a tubing) may be inserted in a septum of an intravenous port, connected by a catheter to a vein (e.g., a Portacath). Ports may be used, for example, to treat hematology and oncology patients.

In some embodiments, a dissolved or solution-dispersed chemical (e.g., an active pharmaceutical ingredient) may be delivered to a tissue of a subject (e.g., subcutaneously, intravenously, intraperitoneally, and/or intrathecally). In some embodiments, a medication delivery system may be of a type that delivers insulin stored in a remote reservoir connected by the tubing to a cannula, or in a unit that is skin mounted or attached with its cannula connected by a short tubing. In some embodiments, the volume of a fluid delivery system (e.g., a medication infusion system) may be smaller than about 100 $cm^3$, for example, smaller than about 20 $cm^3$, and, for example, smaller than about 10 $cm^3$, for example, smaller than about 5 $cm^3$. In some embodiments, a reservoir may contain a sufficient volume of drug solution or dispersion for about 1-10 day therapy, in some cases about 2-3 day therapy, and often about 1 day therapy.

A delivery fluid may comprise, according to some embodiments, a biological and/or chemical material. For example, a delivery fluid may comprise an active pharmaceutical ingredient (API) (e.g., a drug). A delivery fluid may be or may comprise an API as or in a solution, a suspension, and/or an emulsion in some embodiments. A delivery fluid may comprise one or more excipients (e.g., pharmaceutically acceptable excipients). For example, a delivery fluid may comprise any pharmaceutically acceptable vehicle for an API. A non-aqueous vehicle may comprise, in some embodiments, vegetable oils, polyethylene glycols, esters (e.g., ethyl oleate) and the like. A vehicle may comprise, in some embodiments, one or more antibacterial preservatives, antioxidants, tonicity agents, buffers, stabilizers, and/or other components.

An API may be and/or may comprise, according to some embodiments, an opioid narcotic (e.g., fentanyl, remifentanyl, sufentanil, morphine, hydromorphone, oxycodiene and salts thereof); a non-steroidal antinflamatory (NSAID) (e.g., diclofenac, naproxen, ibuprofen, and celecoxib); a local anesthetic (e.g., lidocaine, tetracaine, and bupivicaine); a dopamine agonist (e.g., apomorphine, rotigotine, and ropinerole); drugs used for the treatment and/or prevention of allergies (e.g., an antihistamine, an antileukotriene, an anticholinergic, and an immunotherapeutic agent); an antispastic (e.g., tizanidine and baclofin); a vitamin (e.g., niacin); Selegiline; rasagiline; and any combination thereof. A biological material may be or may comprise a protein, a peptide, a nucleic acid (e.g., an oligonucleotide), a lipid, and/or a carbohydrate.

In some embodiments, a pump system may administer a combination of two or more APIs. For example, a pump system may be configured to include a single delivery fluid chamber filled with the combination. A pump system may be configured, for example, to include two or more delivery fluid chambers that feed into a common catheter/needle or separate catheters/needles. In some embodiments, a pump system may be configured to deliver two or more APIs at a fixed ratio and/or a variable ratio. A pump system may be configured to delivery each API subject to independent delivery modulation in some embodiments. For example, two or more drugs may be administered simultaneously and/or sequentially (e.g., overlapping).

A fluid delivery system may operate, in some embodiments, by indirect pumping. For example, a pump fluid (e.g., a solution containing little or no drug to be delivered, such as deionized water) may pass through a pump, whereas a delivery fluid does not, but instead is pushed by a pump fluid. In some embodiments, a separator may be a displaceable and/or deformable water insoluble solid, a water-immiscible liquid, and/or a water-immiscible gas (e.g., air) preventing the mixing of a pump fluid and a delivery fluid.

In some embodiments, control (e.g., strict control) of a dosage and dose-rate (i.e., delivered volume and flow rate) may be desired and/or required. In some embodiments, a flow rate may be controlled by a constant voltage supply. In some embodiments, a flow rate may be controlled by a constant pressure. In some embodiments, flow rate may be controlled by an applied current. In some embodiments, flow rate may be controlled by an applied voltage. In some embodiments, a flow rate may be continuous. In some embodiments, electrode mass and/or consumption of an anode and/or cathode may allow for 7 hours of continuous operation at a flow rate of 15 μL/min. In some embodiments, an average flow rate may be controlled by pulsing (e.g., periodic voltage and/or current pulsing). For example, flow rate may be controlled by pulsing over a period of about 4 days, about 3 days, about 2 days, about 1 day, about hourly, every about 50 minutes, every about 40 minutes, every about 30 minutes, every about 20 minutes, every about 10 minutes, every about 5 minutes, every about 2 minutes, every about 1 minute, every about 20 seconds. In some embodiments, an average flow rate of 0.13 μL/min may be obtained by applying 10 second pulses of 75 μA, every 15 minutes.

In some embodiments, application of a current (or voltage) across electrodes of a pump may drive protons to the cathode, where they may be consumed by a cathodic reaction. Without being limited to any particular mechanism of action, protons may propagate rapidly at the polyanionic surface of a ceramic membrane dragging the proximal water sheet, which transfers momentum to the water-bulk causing its flow. In some embodiments, (e.g., where electro-osmotic flow is driven by a fast proton flux at the surface of a sandwiched porous membrane and/or adsorption of an impurity on the membrane perturbs flux) it may be desirable to use pure protic liquids like water as a pump fluid.

In some embodiments, an electro-osmotic flow is driven by a fast proton flux at the surface of a sandwiched porous membrane. In some embodiments, a delivery fluid is pushed by pumped water. In some embodiments, dilution of a delivery fluid solution by pumped water is avoided by a separator (i.e., an oil drop and/or a gas bubble) inserted between a water and delivery fluid. In some embodiments, to prevent a separator (e.g., oil drop) from reaching the subcutaneous tissue, the volume of a pump fluid (or pump fluid+pump chamber separator) may be less (e.g., about 0.5 mL less, about 0.2 mL less, and/or about 0.1 mL less) than that of delivery fluid (or delivery fluid+delivery chamber separator). In some embodiments, delivery fluid (e.g., water) in a delivery fluid chamber may become exhausted and separator (e.g., oil) may enter a pump, whereupon flow may be reduced and/or stopped. At that time, some delivery fluid may remain in a delivery fluid chamber. It may be desirable, in some embodiments, for the volume of delivery fluid remaining to be as small as possible or as small as possible without compromising safety.

In some embodiments, a separator may comprise a gas, a liquid and/or a solid. A gaseous separator, in some embodiments, may comprise an air bubble. In some embodiments, an example of a useful liquid separator may be a silicone oil or a glycerol mono or di-ester of a fatty acid. In some embodiments, solid separators may be plastic, ceramic or metallic. In some embodiments, a separator moves along a defined path when pushed by a pumped solution. In some embodiments, a solid separator may optionally also serve in stopping the flow when the delivery fluid is nearly or completely exhausted, for example, by plugging an orifice through which the delivery fluid enters the tubing connected to the body-inserted cannula. In some embodiments, for example, the downstream side of the plug can be conical, the tip of the cone penetrating the cannula or its upstream extension when the delivery fluid is exhausted. In some embodiments, combined volumes of a pumped solution and a delivery fluid may be minimized by making their volumes about similar, with the volume of a delivery fluid exceeding the volume of a pumped solution, so as to avoid delivery of only a pumped solution to the cannula.

Figure 10A:
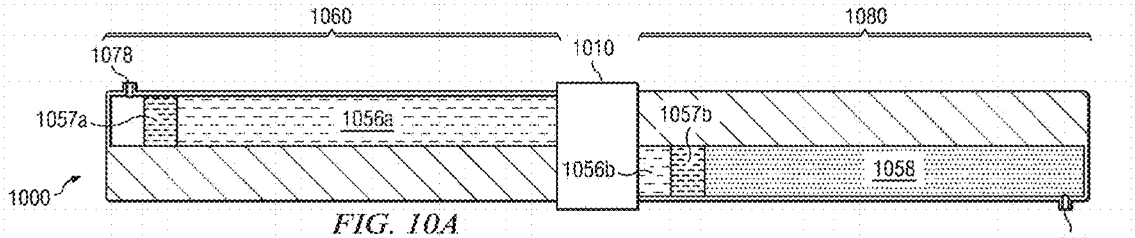
FIG. 10A illustrates a sectional view of a pump system in which the water chamber and the drug chambers are loaded and ready for use according to a specific example embodiment of the disclosure.
Figure 10B:
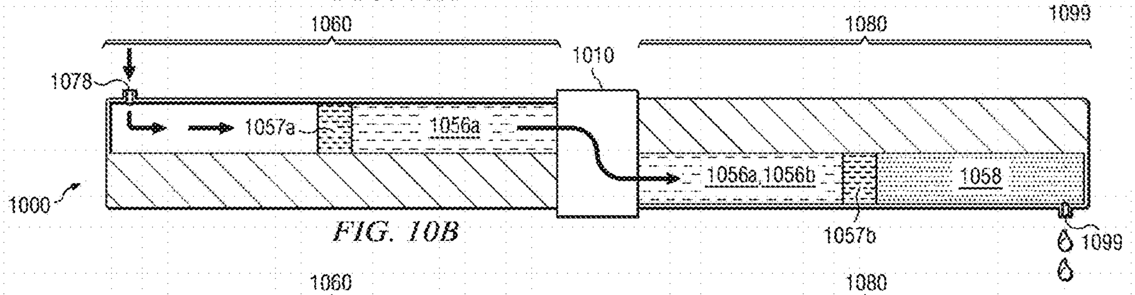
FIG. 10B illustrates a sectional view of the pump system shown in FIG. 10A during operation according to a specific example embodiment of the disclosure.
Figure 10C:
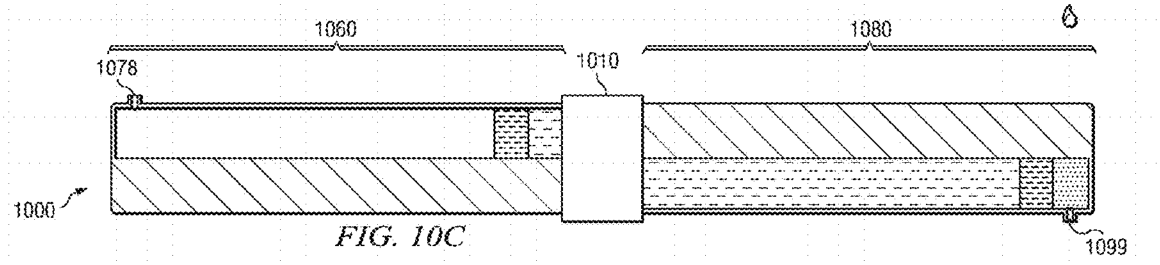
FIG. 10C illustrates a sectional view of the pump shown in FIGS. 10A and 10B following operation according to a specific example embodiment of the disclosure.
Figure 12A:
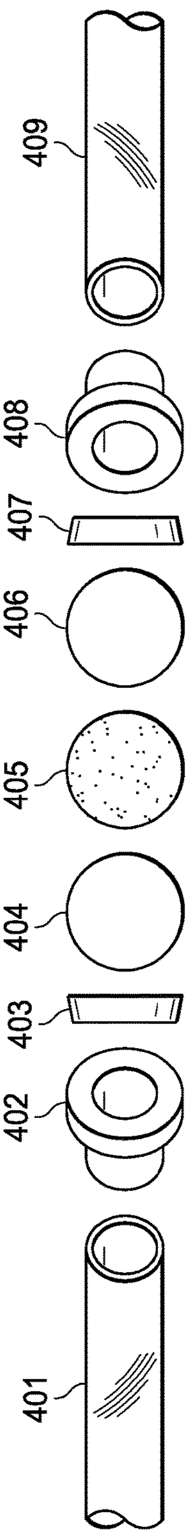
FIG. 12A illustrates a exploded view of a pump according to a specific example embodiment of the disclosure.
Figure 12B:
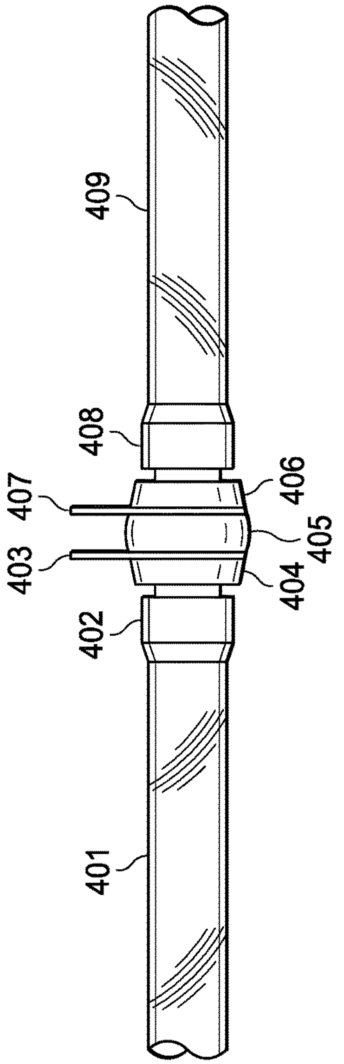
FIG. 12B illustrates the pump shown in FIG. 12A assembled according to a specific example embodiment of the disclosure.

FIGS. 10A-10C illustrate pump system 1000 in operation in which pump fluid chamber 1060 and delivery fluid chamber 1080 have been rendered, for illustration purposes, as coplanar with each other and with pump 1010 similar to the collinear arrangement shown in FIGS. 6A, 7A-7C, and 8A-8E. Pump fluid chamber 1060 and delivery fluid chamber 1080 may be configured as illustrated or may be configured such that pump fluid chamber 1060 substantially overlays delivery fluid chamber 1080 and the two together define, at least partially, an oval and/or a circle (e.g., as shown in FIGS. 4B-4D).

FIG. 10A illustrates a sectional view of pump system 1000 in which the chambers 1060 and 1080 are loaded and ready for use according to a specific example embodiment of the disclosure. FIG. 10B illustrates a sectional view of a pump system shown in FIG. 10A during operation according to a specific example embodiment of the disclosure. Upon application of a potential difference or current across pump 1010, pump fluid 1056*a* begins to flow through pump 1010 into delivery fluid chamber 1080. Separator 1057*a* moves in tandem with the distal edge of pump fluid 1056*a* and air is drawn into chamber 1060 through inlet 1078. As pump fluid 1056*a* moves to and accumulates in chamber 1080, the combined volume of 1056*a* and 1056*b* forces separator 1057*b* to move distally toward outlet 1099, which in turn, expresses delivery fluid 1058 through outlet 1099. FIG. 10C illustrates a sectional view of pump system 1000 near completion of operation according to a specific example embodiment of the disclosure. Flow may be slowed and/or stopped by reducing the potential difference and/or current applied to pump 1010 (e.g., to about zero). In FIG. 10C, flow is stopped with some delivery fluid still remaining in chamber 1080.

In some embodiments, an electro-osmotic pump may comprise (i) one or more phosphorus-containing membranes (e.g., a phosphosilicic acid on silica membrane) and/or boron-containing membranes (e.g., a borosilicic acid on silica membrane), (ii) a non-gassing (e.g., absence of gas bubbles visible to the naked eye), electrooxidizable and proton-generating porous anode constituent (e.g. $Ce^{3+}$), and/or (iii) a non-gassing, hydroxide anion generating or proton-consuming cathode constituent (e.g. $Ce^{4+}$). When operated at low voltages, where no gas evolution causing electrolysis takes place, a pump may provide, in some embodiments, sufficient flow rates for the delivery of drugs (e.g., prandial insulin) and/or pumping cooling fluids, for example, to cool electronic and/or optical devices. According to some embodiments, a low voltage is a voltage of less than about 3 V, for example less than 2.0 V, less than 1.5 V, less than 1.0 V, less than 0.8 V, less than 0.6 V, about 0.5 V or less.

According to some embodiments, a DC electro-osmotic pump may operate at a voltage of less than about 3 V (e.g., less than 1.23 V which is the thermodynamic voltage for the electrolysis of water) at about 25° C. A pump may comprise, for example, a porous, phosphorus containing membrane, for example a membrane made of phosphosilicic acid coated, fused silica microspheres. Flow of deionized water may start at about 0.1 V and may increase about linearly with the applied current. The flow rate may be sufficient, for example, for prandial insulin administration (e.g., bolus delivery).

In some embodiments, electrodes may be re-charged (i.e., the anode made into the cathode and vice versa). For example, the electrodes may be rotated by reversing the current, so that the $Ce^{3+}$ formed at the cathode in the operating pump from $Ce^{4+}$ may be re-oxidized, while the $Ce^{4+}$ formed at the cathode in the operating pump from $Ce^{3+}$ may be re-reduced.

To control their blood sugar levels, Type 1 diabetic people need about 0.8 insulin units/kg/day. There are about 27 units in 1 mg of insulin, and fast acting insulin solutions contain typically about 100 units/mL. The dosings and timings of insulin vary from patient to patient. In the management of Type 1 diabetes, in some patients, about ¼ of the insulin, i.e., about 0.2 insulin units/kg/day, are continuously administered, and about 0.2 insulin units/kg are administered with each of the three daily meals. In the case of a person weighing 80 kg, about 16 units, i.e., about 160 μL of fast acting insulin are delivered with a meal. For a 20 minute delivery the required pumping rate is about 8 μL/min.

Allergen Diagnostics

According to the website of the NIH-National Institute of Allergic Diseases, allergies are the sixth leading cause of chronic disease in the United States. Their 2005 cost to the healthcare system was about $18 billion. About half of all Americans test positive for at least 1 of the 10 most common allergens: Ragweed, bermuda grass, rye grass, white oak, Russian thistle, alternaria mold, cat, house dust mite, German cockroach, peanut. Food allergy occurs in 6-8% of children younger than 6 and in 2% of adults. Common food allergens include: Cow's milk; eggs; shellfish; nuts. In 2005, 30 million people living in the United States had asthma, resulting in >480,000 hospitalizations and about 4,200 deaths.

Figure 11:
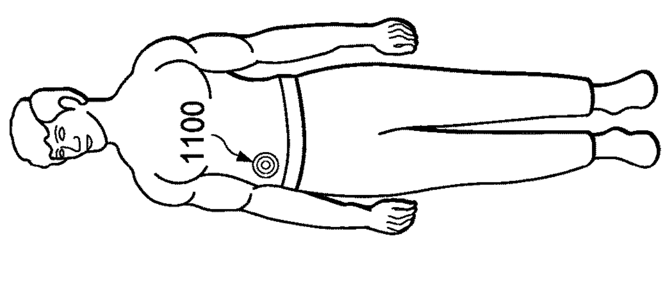
FIG. 11 illustrates a subject wearing a pump system according to a specific example embodiment of the disclosure.
Figure 13B:
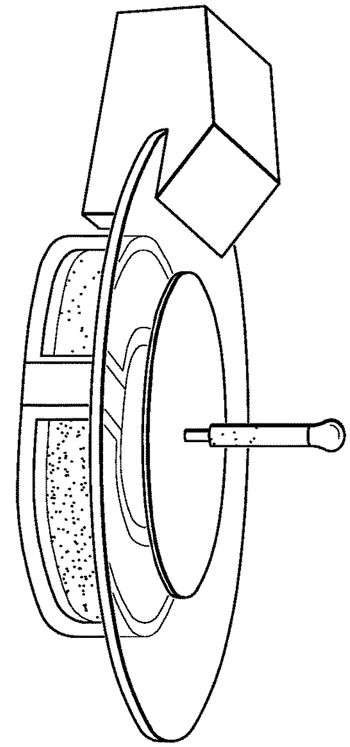
FIG. 13B illustrates a generally isometric view of the pump system shown in FIG. 13A in operation such that fluid has begun to move through drug outlet according to a specific example embodiment of the disclosure.
Figure 13D:
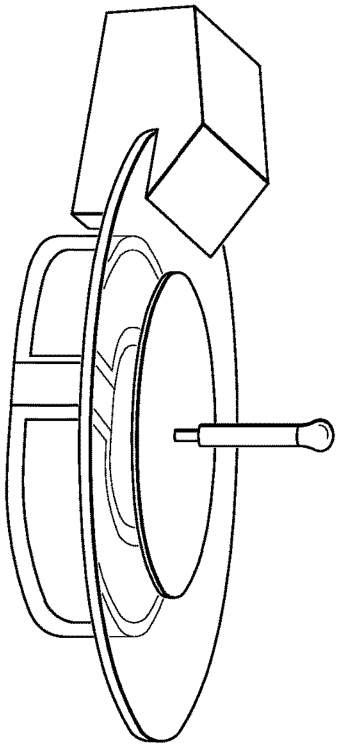
FIG. 13D illustrates a generally isometric view of the pump system shown in FIGS. 13A-13C in which fluid movement through drug outlet has been stopped according to a specific example embodiment of the disclosure.
Figure 13A:
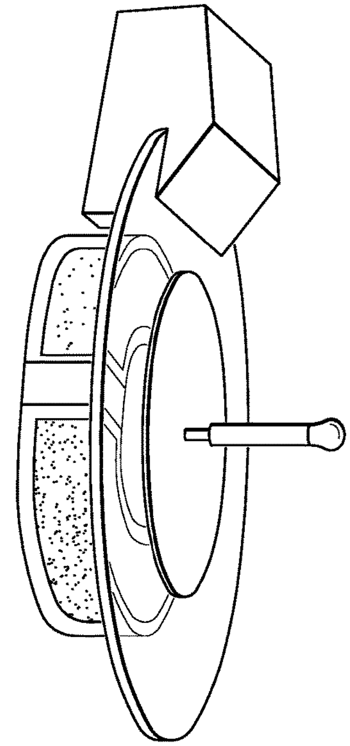
FIG. 13A illustrates a generally isometric view of a pump system according to a specific example embodiment of the disclosure.
Figure 13C:
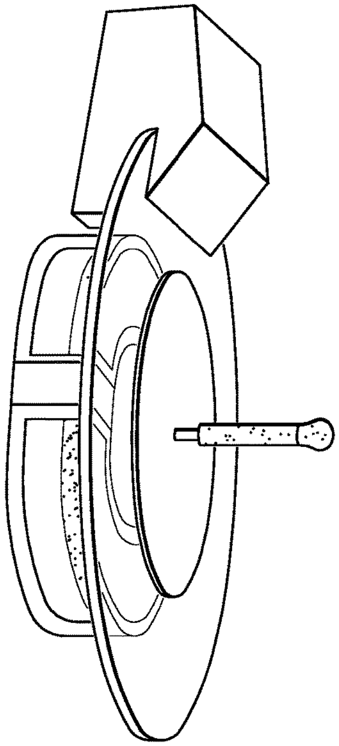
FIG. 13C illustrates a generally isometric view of the pump system shown in FIGS. 13A-13B in which fluid continues to move through drug outlet according to a specific example embodiment of the disclosure.
Figure 14:
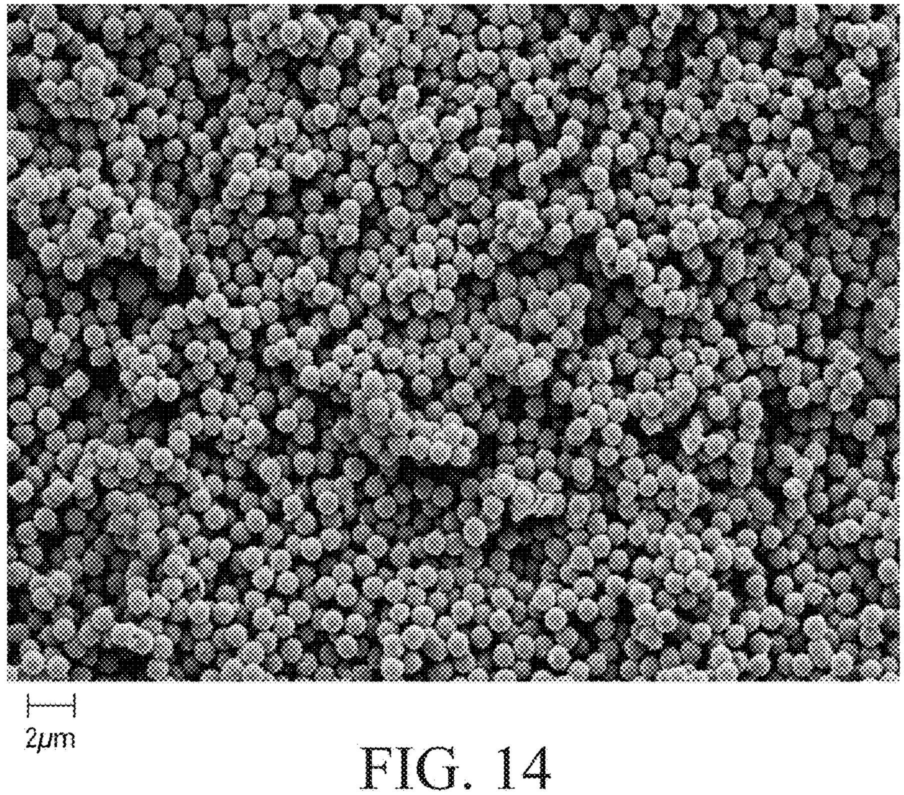
FIG. 14 is a scanning electron micrograph that illustrates a pump membrane according to a specific example embodiment of the disclosure.

According to some embodiments, a fluid delivery system (e.g., electro-osmotic pumps) may also be used (e.g., advantageously used) in immunotherapy of allergies. According to present practice, a series of increasingly concentrated suspensions or solutions of the allergen or allergens to which the patient is sensitive are subcutaneously injected. The suspensions are administered over an extended period of time, typically several years. The injections are believed to reduce the level of IgE antibodies in the blood and to cause the body to make protective IgG antibodies. In present practice the patient needs to visit the office of the allergist, wait to be injected by a nurse or other health professional, and then wait at least about 20 min to assure the absence of a severe allergic reaction to the administered dose. The dosing is usually sub-optimal, because the allergist wishes to be reasonably certain that there will not be a severe allergic reaction. Gradual delivery of the suspension or solution over a period longer than about 5 minutes (e.g., longer than about 10 min, longer than about 30 min, longer than about 1 hour, longer than about 3 hours, and/or longer than about 6 hours) would allow a subject to remove a skin-adhered system containing an electro-osmotic or other drug pump if he or she observes excessive reddening or swelling indicative of the start of an unwanted excessive allergic reaction. Such an allergy immunotherapy system may have, other than the pump itself, two small compartments, of similar or different volumes. Each compartment may, independently, have a volume of, for example, less than about 2 mL, less than about 1 mL, less than about 0.5 mL, and/or less than about 0.2 mL. One compartment may contain a pumped solution, (e.g., de-ionized water or water containing less than about $10^{-2}$ moles per liter of a solute) and/or a second compartment may contain a suspension or solution of one or more allergens. The two compartments may be separated by a moving separator, which may be moved by a pumped solution (e.g., de-ionized water), and push an allergen-containing suspension. A system may also comprise means to attach it to the skin, such as a non-allergic two sided adhesive tape used by wearers of wigs and hairpieces, and a short hollow needle, which may be, for example, longer than about 0.1 cm and shorter than about 0.6 cm and/or longer than about 0.3 cm and shorter than about 0.5 cm. FIG. 11 illustrates a subject wearing a pump system an according to a specific example embodiment of the disclosure. A needle may be narrow (e.g., between about 24 and about 33 gauge and/or between about 26 gauge and about 30 gauge). A needle may be connected directly to the drug reservoir or it may be connected to the drug reservoir through tubing, for example plastic tubing. A pump may also be used to administer one or more vaccines.

Allergists now use skin tests to determine whether a person has IgE antibodies in the skin that react to a specific allergen. In these skin tests they inject subcutaneously, or apply to a scratch, series of about constant volumes of extracts of decreasingly diluted allergens, such as dust mites, pollens, or molds found in the area in which the patient lives or works. In a positive reaction, a small, raised, reddened wheal, with a surrounding flare, appears at the test site. The inverse of the dilution of the injected allergen extract, its volume and size of the wheal allow the allergist to gauge the relative sensitivity of a person to different allergens.

According to some embodiments of the disclosure, the tested allergen containing suspension or solution may be subcutaneously administered by pumping, for example by a system comprising the disclosed electro-osmotic pump. It may be administered, for example, at a fixed flow rate (e.g., between about 0.1 μL $min^{-1}$ and about 10 μL $min^{-1}$ and/or between about 0.5 μL $min^{-1}$ and about 0.5 μL $min^{-1}$) until the positive reaction indicative flare or wheal or combination of flare and wheal is observed, when the flow would be stopped. The inverse elapsed timed between the start of the flow and the stopping of the flow would indicate the sensitivity to the tested allergen. Alternatively, the flow rate would be increased during the test, for example in 0.1 μL $min^{-1}$ increments, until the flare or wheal or combination of flare and wheal is observed and the flow is stopped, for example, by removing the system. The inverse number of increments between the starting of the flow and its stopping would indicate the sensitivity to the tested allergen. Alternatively, small boluses may be intermittently administered. Boluses may be of constant or increasing volume. In some embodiments, they would be larger than about 100 nL and smaller than about 10 μL. They may be delivered about every 2 minutes or less, for example every minute or less, for example every 30 s or less, for example every 10 s or less.

In a diagnostic system, the combined volumes of an allergen suspension or solution, a pumped aqueous solution and a pump itself may total, according to some embodiments, less than about 5 mL, less than about 2 mL, less than about 1 mL, and/or less than about 0.5 mL. In some embodiments, a system may have a generally circular and/or annular shape with a diameter of, for example, less than about 2 cm, less than about 1 cm, less than about 6 mm, less than about 4 mm. According to some embodiments, an electro-osmotic pump system may be skin-attached, optionally off the site of the administration of the tested allergen, so as not to block the view of the expected wheal and flare. A system may be worn, in some embodiments, for a period longer than about 2 min, longer than about 5 min, longer than about 10 min, longer than about 30 min, and/or until a positive reaction indicative flare is observed. Flow may then be stopped and the system would be optionally removed from the skin. Optionally, the flow would be automatically stopped and the elapsed time or number of boluses measured when the flare or the wheal develop. For such automatic monitoring or control of flow, a system may also comprise a detector or multiple detectors, for example of reflected light or of temperature. Development of the flare may be tracked for example by reflectometry or thermometry. For example, the ratio of the reflected light of wavelengths between about 600 and about 900 nm to that reflected between about 400 nm and about 900 nm may be monitored to track the reddening. Alternatively, the decrease in the reflected flux of white or yellow light may be monitored; or the temperature difference between the core of the flare and a nearby skin site but off the flare may be monitored.

A diagnostic system may have, other than the pump itself, two small compartments, of similar or different volumes. Each compartment may, independently, have a volume of, for example, less than about 2 mL, less than about 1 mL, less than about 0.5 mL, and/or less than about 0.2 mL. A system may also comprise a hollow needle, which may be, for example, longer than about 2 mm and shorter than about 1 cm and/or longer than about 3 mm and shorter than about 6 mm. A needle may be narrow (e.g., between about 24 and about 33 gauge and/or between about 26 gauge and about 30 gauge). A needle may be connected, for example through plastic tubing, to an allergen suspension or solution containing reservoir. Tubing, part of which may be taped to the skin, may be long enough to permit subcutaneous delivery of the allergen suspension or solution at a site not covered by a reservoir and pump comprising system. In some embodiments, tubing may be longer than about 1 cm, longer than about 3 cm, and/or longer than about 5 cm. A needle may be inserted below the skin at an off-vertical angle for shallow penetration and delivery of the allergen optionally in the outer part of the dermis that is proximal to the epidermis. For example, a needle may be inserted at an angle (versus vertical) of at least about 50°, at least about 60°, at least about 70°, and/or at least about 80°.

In some embodiments, a system may also comprise a factory or health care professional programmed electronic system controlling the flow rate and monitoring the delivered dose of the allergen. This system may be optionally incorporated, as shown for example in FIG. 6C, in the skin attached package. Unlike a drug reservoir, pumped aqueous solution reservoir and/or an electro-osmotic pump of a system, which may be discarded after use, an electronic control and display system may be separable, removable, and/or reusable. An electronic control and display system may be electrically connected to an electro-osmotic pump through contact pads, which both the re-used electronic control unit and the pump may have. Optionally, for safety, an electronic part of a system may provide a periodic alarm, alerting a patient or health care professional to check the inflammatory response such as a wheal or flare. It may discontinue flow of allergen solution or suspension unless a patient or health care provider confirms that the inspection did not show as yet sufficient inflammatory response. The periods between the alerts may be fixed and/or user-selectable. For example, the period between alerts may be less than about 20 min, less than about 10 min, less than about 5 min, and/or less than about 2 min.

Immunotherapy, typically involving weekly or twice-weekly subcutaneous allergen injections for three years, provides relief after 1 year to 85% of the patients. Inexpensive drug pumps in general and particularly single-use electro-osmotic pumps may be advantageously used in the immunotherapy of allergies. According to the present practice of immunotherapy, a series of increasingly concentrated suspensions or solutions of the allergen or allergens to which the patient is sensitive is subcutaneously injected. The solutions or suspensions are administered over an extended period of time, typically several years. The injections are believed to reduce the level of IgE antibodies in the blood and to cause the body to make protective IgG antibodies. According to the present practice, the patient needs to visit the office of the allergist, wait to be injected by a nurse or other health professional, and then wait at least about 20 min to assure the absence of a severe allergic reaction to the administered dose. The dosing is usually sub-optimal, because the allergist wishes to be reasonably certain that there will not be a severe allergic reaction. Delivery of the allergen suspension or solution over a period longer than about 5 min, for example longer than about 10 min, for example longer than about 30 min, for example longer than about 1 hour, for example longer than about 3 hours, for example longer than 6 hours would allow the patient to remove the skin-adhered system containing the electro-osmotic or other drug pump when he or she observes excessive response, such as excessive reddening or swelling.

An immunotherapy system of this disclosure is designed to deliver an about optimal and always safe dose of the allergen or allergens. Some, but not all components and functions may be similar to those of the diagnostic system. Because the delivery of the therapeutic doses may be generally in the dermis or in the tissue below the dermis, such as adipose tissue or connective tissue or muscle, the needle may be inserted about vertically to the skin, for example at an angle of at least about 60° versus the plane of the skin, for example at least about 70° versus the plane of the skin, for example at least about 80° versus the plane of the skin. The solution or suspension of the allergen or allergens may be administered for example until a sufficient but not excessive local inflammatory response is observed, exemplified by the appearance of a red, about circular, region, of a diameter typically greater than about 2 mm and less than about 2 cm, typically greater than about 4 mm and less than about 1 cm, or by local swelling, or by local itching. Flow rate may be adjusted such that the inflammatory response may be projected to appear more than about 5 min after the start of the flow, for example more than about 10 min, for example more than about 20 min, for example more than about 30 min, for example more than about 1 hour, for example more than about 2 hours, for example more than about 3 hours, for example more than about 6 hours. When the inflammatory response is observed, the delivery of the allergen comprising solution or suspension may be discontinued and the system may be removed from the skin.

A hollow needle 506 may be placed, as shown in FIG. 6C, below the skin attached system and covered by it. In some embodiments, a hollow needle may be placed in a region other than where the package is adhered to the skin, for example, to allow visual inspection for the appearance of a flare or wheal or for visual confirmation that the needle is properly implanted. A system may also comprise a hollow needle, which may be, for example, longer than about 2 mm and shorter than about 1 cm and/or longer than about 3 mm and shorter than about 5 mm. A needle may be narrow (e.g., between about 24 and about 33 gauge and/or between about 26 gauge and about 30 gauge). It may be connected to the allergen containing reservoir for example by a sufficiently long plastic tubing to allow easy observation of the evolution of the inflammatory response at the delivery site. An immunotherapy system may have, other than the pump itself, two compartments, of similar or different volumes. Each compartment may, independently, have a volume of, for example, less than about 2 mL, less than about 1 mL, less than about 0.5 mL, and/or less than about 0.2 mL.

A system may also comprise a factory or health care professional programmed electronic system controlling the flow rate and monitoring the delivered dose of the allergen. This system may be optionally incorporated, as shown for example in FIG. 6C, in the skin attached package. Unlike the drug reservoir, pumped aqueous solution reservoir and electro-osmotic pump part of the system, which would be typically discarded after use, the electronic control and display system would be removable and reusable. It may be connected to the pump through contact pads, which both the re-used electronic control unit and the typically disposable solution and pump containing part would have. Optionally, for safety, the electronic part of the system may provide a periodic alarm, telling the patient or health care professional to inspect the extent of the wheal or flare. It may discontinue delivery of the allergen solution or suspension unless the patient or health care confirms the inspection. The periods between the alarms may be typically of about less than 20 min, for example less than 10 min, for example less than 5 min, for example less than 2 min.

As will be understood by those skilled in the art who have the benefit of the instant disclosure, other equivalent or alternative compositions, devices, methods, and systems for pumping a fluid (e.g., an active pharmaceutical ingredient, an allergen, a nutrient, a diagnostic agent) can be envisioned without departing from the description contained herein. Accordingly, the manner of carrying out the disclosure as shown and described is to be construed as illustrative only.

Persons skilled in the art may make various changes in the shape, size, number, and/or arrangement of parts without departing from the scope of the instant disclosure. For example, the position and number of a pump, cathode, anode electrodes, tubing, PVC frames, PVC rings, reservoir, reservoir chambers, hairpins, curvatures, controller, air gaps, drug inlets, drug outlets, oil gaps, controller, processor, memory, power source, display, user interface, needle, adhesive, elastic band, and/or wires may be varied. In some embodiments, pump, cathode, anode electrodes, tubing, PVC frames, PVC rings, reservoir, reservoir chambers, hairpins, curvatures, controller, air gaps, drug inlets, drug outlets, oil gaps, controller, processor, memory, power source, display, user interface, needle, adhesive, elastic band, and/or wires may be interchangeable. In addition, the size of a device and/or system may be scaled up (e.g., to be used for adult subjects) or down (e.g., to be used for juvenile subjects) to suit the needs and/or desires of a practitioner. Each disclosed method and method step may be performed in association with any other disclosed method or method step and in any order according to some embodiments. Where the verb "may" appears, it is intended to convey an optional and/or permissive condition, but its use is not intended to suggest any lack of operability unless otherwise indicated.

Also, where ranges have been provided, the disclosed endpoints may be treated as exact and/or approximations as desired or demanded by the particular embodiment. Where the endpoints are approximate, the degree of flexibility may vary in proportion to the order of magnitude of the range. For example, on one hand, a range endpoint of about 50 in the context of a range of about 5 to about 50 may include 50.5, but not 52.5 or 55 and, on the other hand, a range endpoint of about 50 in the context of a range of about 0.5 to about 50 may include 55, but not 60 or 75. In addition, it may be desirable, in some embodiments, to mix and match range endpoints. Also, in some embodiments, each FIGURE disclosed (e.g., in one or more of the examples, tables, and/or drawings) may form the basis of a range (e.g., depicted value+/−about 10%, depicted value+/−about 50%, depicted value+/−about 100%) and/or a range endpoint. With respect to the former, a value of 50 depicted in an example, table, and/or drawing may form the basis of a range of, for example, about 45 to about 55, about 25 to about 100, and/or about 0 to about 100. Persons skilled in the art may make various changes in methods of preparing and using a composition, device, and/or system of the disclosure. For example, a composition, device, and/or system may be prepared and or used as appropriate for animal and/or human use (e.g., with regard to sanitary, infectivity, safety, toxicity, biometric, and other considerations).

All or a portion of a device and/or system for electro-osmotic pumping may be configured and arranged to be disposable, serviceable, interchangeable, and/or replaceable. These equivalents and alternatives along with obvious changes and modifications are intended to be included within the scope of the present disclosure. Accordingly, the foregoing disclosure is intended to be illustrative, but not limiting, of the scope of the disclosure as illustrated by the claims below.

The title, abstract, background, and headings are provided in compliance with regulations and/or for the convenience of the reader. They include no admissions as to the scope and content of prior art and no limitations applicable to all disclosed embodiments.

EXAMPLES

Some specific example embodiments of the disclosure may be illustrated by one or more of the examples provided herein.

Example 1: Pump Membrane

An exemplary membrane was made by (a) adding 5 μL of 85 wt. % $H_3PO_4$ to 5.0 mL of a 10 wt % suspension of 1 μm diameter monodisperse silica microspheres (Polysciences, Warrington, Pa., Cat. #24326-15); (b) evaporating the water at 65° C.; (c) placing 65 mg of the resulting dried powder in an 8 mm die and hand-pressing to form a pellet; and (d) firing the pellet for 4 h at 700° C. The membrane was then washed with a sufficient volume of water to remove any unbound $H_3PO_4$ and dried. The 1.3 mm thick membrane consisted of randomly packed microspheres.

Example 2: Electrodes Comprising Cerium Oxide

Cerium oxide comprising electrodes of an electro-osmotic pump were prepared as follows: Carbon paper (3.6 cm×1.8 cm (6.5 $cm^2$) sheet of 130 μm thick, 78% porosity carbon paper (from Toray)) was used as the base material and the carbon paper was plasma-treated, with a low pressure (about 20 Torr or less) air plasma for about 45 min. Timcal Super C45 carbon (from Timcal USA, Westlake, Ohio), was made hydrophilic by treating it with colloidal tin oxide. The tin oxide treatment consisted of (a) mixing 100 mL distilled water, 1 mL 15 weight % colloidal tin oxide (SN 15, Nyacol Technologies Inc.) and 100 mg of Triton X-100 (Sigma-Aldrich), then adding to the stirred mixture 2 g of the Timcal Super C45 carbon and continuing the stirring was for 1 hour. The solid was collected by filtration; the collected cake was dried at 70° C. for 6 hours, transferred to a silica crucible, heated, with the temperature increased at a rate of about 10° C./min to 320° C., then firing at 320° C. for 10 min, cooling, washing with distilled water and drying at 70° C. for 6 hours.

An about homogeneous cerium oxide-comprising paste was prepared by mixing of 2 mL 5% NAFION solution (Sigma-Aldrich), 8 mL isopropanol (Sigma-Aldrich), 500 μL colloidal ceria sol [CEO2(AC) or CEO2(NO3) Nyacol Technologies Inc., Ashland, Mass.] and 100 mg carbon (Timcal Super-C45). Prior to its mixing with carbon, the colloidal ceria sol was oxygenated for by passing through it gaseous $O_2$ for 10 min. The cerium oxide containing paste was applied to a 3.6 cm×1.8 cm (6.5 $cm^2$) sheet of 130 μm thick, 78% porosity carbon paper (Toray Carbon) by dipping the carbon paper in the paste, removing it from the paste and drying it at about 70° C. After drying, the now coated carbon paper was cleansed by boiling water and cut to form 8 mm diameter circular electrodes.

Example 3: Electrodes without Metallic Conductive Material

Substantially metal-free electrodes of an electro-osmotic pump may be prepared as follows: Carbon paper (from Toray) may be used as the base material and the carbon paper may be plasma-treated, with a low pressure (about 20 Torr or less) oxygen plasma for about 45 min and cut to form 8 mm diameter circular electrodes. Alternatively, a paste of hydrophilic Timcal Super C45 carbon made hydrophilic by plasma treatment may be applied to carbon paper as described in Example 2 except without the colloidal tin oxide treatment. Carbon paper with the applied paste then may be plasma treated and cut as desired to form metal-free electrodes.

Example 4: Pump Assembly and Pre-Conditioning

Assembly and Pre-Conditioning of the Pump.

The anode and the cathode of the pump were similar. The pump was assembled as described in Application WO2011/112723 A2 by sandwiching between two 8 mm diameter electrodes an 8 mm diameter ceramic membrane of about 0.1 $cm^3$ volume and about 2 mm thickness. The assembly was housed between two PVC rings with lips, with thin gold foils inserted between each electrode and the PVC housing-rings for electrical contact. The assembly was then encapsulated in a slow curing (24 h) two-component epoxy resin.

Example 5: Pump Operation

Currents, Voltages and Flow.

Figure 15:
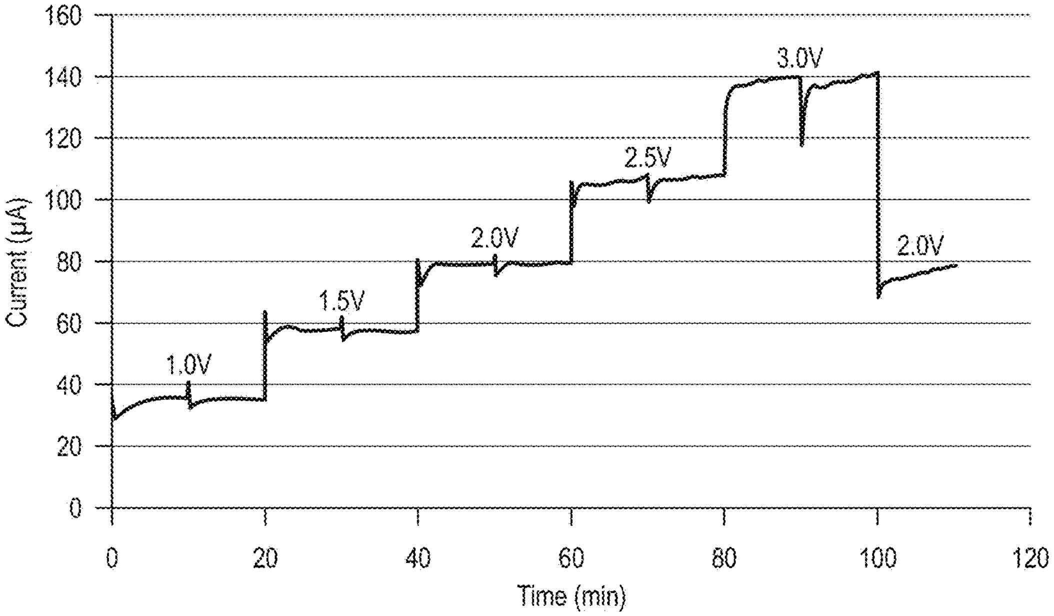
FIG. 15 illustrates the voltage dependence of the flow through a pump having electrodes comprising cerium oxide according to a specific example embodiment of the disclosure.
Figure 16:
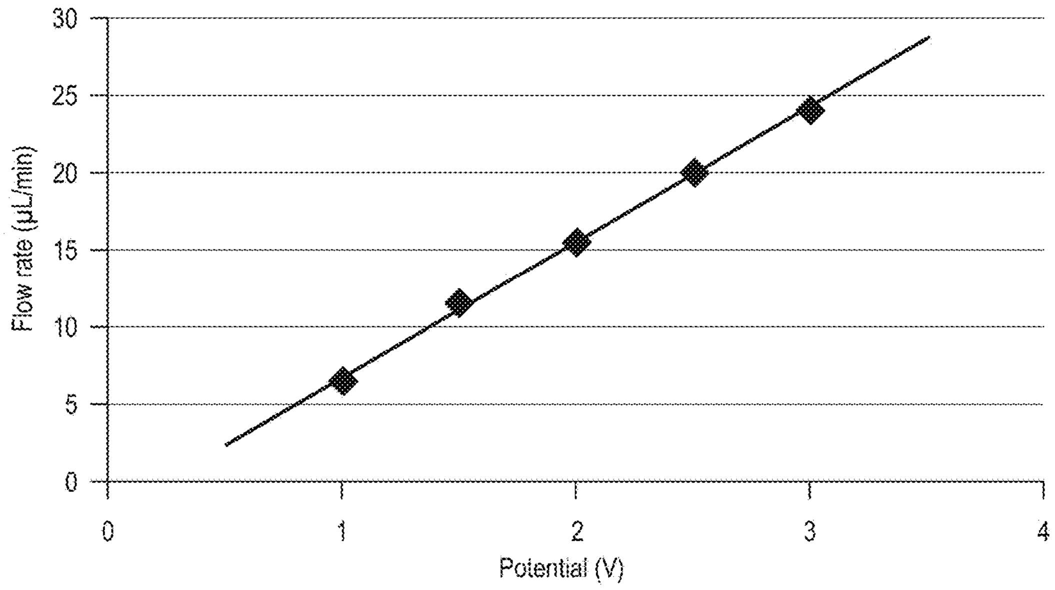
FIG. 16 illustrates a linear increase in flow with the applied voltage for a pump having electrodes comprising cerium oxide according to a specific example embodiment of the disclosure.

The applied voltage dependence of the flow through the pump with the 8 mm OD electrodes and membrane; Because 1 mm wide lips of the PVC rings prevented contact with water at the rim, the effective diameter of the circular water pumping area was 6 mm, i.e. the water-contacting-area electrodes was 0.28 $cm^2$. As seen in FIG. 15 the flow was constant when a particular potential was applied. When 1 V was applied, the flow was about 7 μL/min, or about 25 μL $min^{-1}$ $cm^{-2}$; when 2 V was applied, the flow was about 15 μL/min, or about 54 μL $min^{-1}$ $cm^{-2}$; when 3 V was applied, the flow was about 24 μL/min, or about 86 μL $min^{-1}$ $cm^{-2}$. The discontinuities represent 10 min interruptions in the application of voltage. After each interruption, i.e. when the voltage was re-applied, the flow resumed its pre-interruption rate. The flow increased about linearly with the applied voltage (FIG. 16).

Example 6: Effect of Boiling the Water

Figure 17:
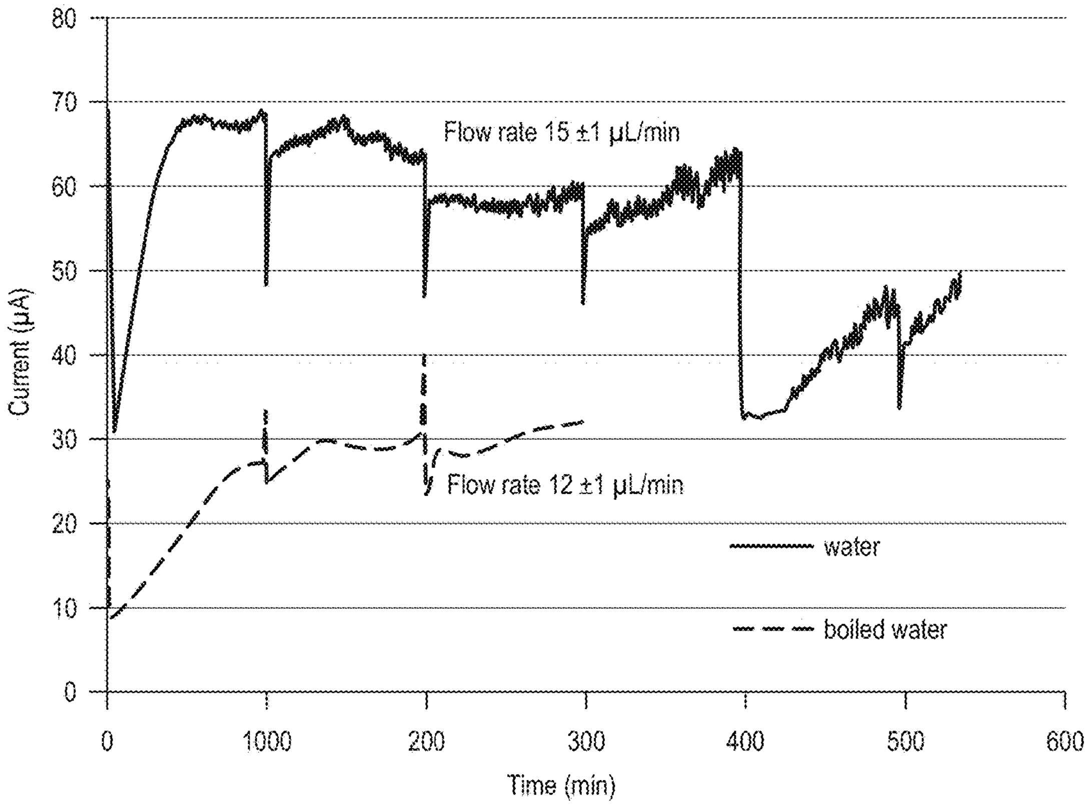
FIG. 17 illustrates changes in current and flow in a pump having electrodes comprising cerium oxide operated at constant voltage and with non-boiled and freshly boiled water according to a specific example embodiment of the disclosure.

As seen in FIG. 17, the current at a constant applied voltage and flow were reduced when the water placed in the pump was freshly boiled; boiling transiently reduced the concentration of the dissolved gases, such as $CO_2$ and/or $O_2$. The discontinuities seen are brief interruptions, after 90 min, in the application of potential. FIG. 17 also shows that a steady current is reached after about 10 min in un-boiled and therefore air-equilibrated water, but it takes about 100 min in boiled water, i.e. in water of which boiling removed the dissolved air and which has not yet fully air-equilibrated.

What is claimed is:

1. A direct current electro-osmotic pump comprising:

a pair of porous electrodes positioned at a distance from each other; and a porous membrane comprising a first side and a second side, wherein each electrode comprises a non-metallic electrochemically reactive component that can gain a proton, gain an electron, lose a proton, lose an electron, or a combination thereof, and at least one electrode further comprises a lanthanide oxide, an actinide oxide, or both;

wherein the membrane is positioned between the pair of electrodes;

wherein at least a part of the first side of the membrane is in physical contact with one of the electrodes, and at least a part of the second side of the membrane is in physical contact with the other electrode wherein both of the electrodes are substantially free of silver, platinum, palladium, nickel, copper, tungsten, molybdenum, alloys thereof, and compounds thereof; and wherein at least one of the electrodes is substantially free of metal.

2. A direct current electro-osmotic pump according to claim 1, wherein the membrane comprises a porous ceramic.

3. A direct current electro-osmotic pump according to claim 2, wherein the porous ceramic comprises silicon.

4. A direct current electro-osmotic pump according to claim 3, wherein the silicon is vitreous silicon dioxide.

5. A direct current electro-osmotic pump according to claim 1, wherein the lanthanide oxide or the actinide oxide comprises an oxide of cerium, an oxide of praseodymium, an oxide of thorium or combinations thereof.

6. A direct current electro-osmotic pump according to claim 1, wherein at least one of the electrodes comprises an oxide of cerium as the lanthanide oxide.

7. A direct current electro-osmotic pump according to claim 1, wherein the membrane is a polymeric-organic membrane comprising a cation exchanger.

8. A direct current electro-osmotic pump according to claim 7, wherein the cation exchanging polymer comprises sulfur atoms.

9. A direct current electro-osmotic pump according to claim 7, wherein the cation exchanging polymer comprises fluorine atoms.

10. A direct current electro-osmotic pump according to claim 7, wherein the cation exchanging polymer comprises perfluorinated polysulfonic acid.

11. A direct current electro-osmotic pump according to claim 1 further comprising a pump fluid.

12. A direct current electro-osmotic pump according to claim 11, wherein the pump fluid comprises water.

13. A direct current electro-osmotic pump according to claim 1, wherein the non-metallic electrochemically reactive component comprises carbon.

14. A direct current electro-osmotic pump according to claim 1, wherein the carbon comprises woven or non-woven carbon cloth or paper, or carbon foam.

15. A direct current electro-osmotic pump comprising:

a porous cathode and a porous anode and a porous ceramic membrane between the cathode and the anode, wherein the porous cathode and the porous anode each comprise a non-metallic electrochemically reactive component that can gain a proton, gain an electron, lose a proton, lose an electron, or a combination thereof, and at least one electrode further comprises a lanthanide oxide, an actinide oxide, or both;

wherein at least a part of the surface of the membrane is in physical contact with the anode and at least a part of the opposite side of the membrane is in physical contact with the cathode;

wherein the porous cathode and the porous anode are each substantially metal free.

16. A direct current electro-osmotic pump according to claim 15, wherein one of the porous cathode and the porous anode comprises cerium oxide as the lanthanide oxide.

17. A direct current electro-osmotic pump according to claim 15, wherein the non-metallic electrochemically reactive component comprises carbon.

18. A direct current electro-osmotic pump according to claim 15, wherein the carbon comprises woven or non-woven carbon cloth or paper, or carbon foam.

19. A direct current electro-osmotic pump according to claim 15, wherein the membrane comprises a porous ceramic.

20. A direct current electro-osmotic pump according to claim 19, wherein the porous ceramic comprises silicon.

21. A direct current electro-osmotic pump according to claim 20, wherein the silicon is vitreous silicon dioxide.

22. A direct current electro-osmotic pump according to claim 15, wherein the lanthanide oxide or the actinide oxide comprises an oxide of cerium, an oxide of praseodymium, an oxide of thorium or combinations thereof.

23. A direct current electro-osmotic pump according to claim 15, wherein the membrane is a polymeric-organic membrane comprising a cation exchanger.

24. A direct current electro-osmotic pump according to claim 23, wherein the cation exchanging polymer comprises sulfur atoms.

25. A direct current electro-osmotic pump according to claim 23, wherein the cation exchanging polymer comprises fluorine atoms.

26. A direct current electro-osmotic pump according to claim 23, wherein the cation exchanging polymer comprises perfluorinated polysulfonic acid.

27. A direct current electro-osmotic pump according to claim 15 further comprising a pump fluid.

28. A direct current electro-osmotic pump according to claim 27, wherein the pump fluid comprises water.

* * * * *